US007842800B2

(12) United States Patent
Bentwich

(10) Patent No.: US 7,842,800 B2
(45) Date of Patent: Nov. 30, 2010

(54) BIOINFORMATICALLY DETECTABLE GROUP OF NOVEL REGULATORY BACTERIAL AND BACTERIAL ASSOCIATED OLIGONUCLEOTIDES AND USES THEREOF

(75) Inventor: Itzhak Bentwich, Kfar Daniel (IL)

(73) Assignee: Rosetta Genomics Ltd., Rehovot (IL)

( * ) Notice: Subject to any disclaimer, the term of this patent is extended or adjusted under 35 U.S.C. 154(b) by 379 days.

(21) Appl. No.: 10/708,951

(22) Filed: Apr. 2, 2004

(65) Prior Publication Data
US 2007/0042982 A1 Feb. 22, 2007

(51) Int. Cl.
*C07H 21/04* (2006.01)
(52) U.S. Cl. .................................. 536/24.5; 536/23.1
(58) Field of Classification Search ................ None
See application file for complete search history.

(56) References Cited

U.S. PATENT DOCUMENTS 5,541,308 A * 7/1996 Hogan et al. ............... 536/23.1
7,300,788 B2 * 11/2007 Matsuzaki et al. ......... 435/287.2
2005/0182005 A1 * 8/2005 Tuschl et al. ................ 514/44

OTHER PUBLICATIONS

Krutzfeldt et al. (2006) Nature Genetics 38:514-519.*
Bentwich et al. (2005) FEBS Lett. 579:5904-5910.*
Martin et al. (2007) J. Biosci. 32:1049-1052.*
Maziere et al. (2007) Drug Discovery Today 12:452-458.*
Smalheiser et al. (2006) Methods Mol. Biol. 342:115-127.*
Bahram et al. (1996) Immunogenetics 44:80-81.*
Buck et al (BioTechniques 27: 528-536, 1999).*
Kim et al. (1996) "Construction and characterization of a human bacterial artificial chromosome library" Genomics 34:213-218.*
GenBank Accession No. AC_011453 "*Homo sapiens* chromosome 19 clone CTC-339O9, complete sequence", as published online Jul. 14, 2002, retrieved from the Nation Center for Biotechnology Information [online] on Sep. 17, 2008 at ncbi.nlm.nih.gov/entrez.*
Online publication at [http://]genome.chop.edu/access/pages/repository/data/chr19/element_to_clone/element_to_clone.txt, retrieved Sep. 17, 2008.*
The International Human Genome Sequencing Consortium (2001) "Initial sequencing and analysis of the human genome" Nature 409:860-921.*
Scherr et al. (2003) Cell Cycle 2:3, pp. 251-257.*
Cullen (2004) "Derivation and function of small interfering RNAs and microRNAs" Viral Res. 102:3-9.*
Brown (1998) "In situ hybridization with riboprobes: An overview for veterinary pathologists" Vet. Pathol. 35:159-167.*
Bauer S, et al. Science, 1999;285:727-9.
Doench JG and Sharp PA. Genes Dev, 2004,18(5):504-11.
Lau NC, et al. Science, 2001;294:858-62.
Lagos-Quintana M, et al. Science, 2001;294:853-8.
Moss EG, et al. Cell, 1997;88:637-46.
Reinhart BJ, et al. Nature, 2000;43:901-6.
Slack FJ, et al. Mol Cell, 2000;5:659-69.
Wightman B, et al. Cell, 1993;75:855-62.
Lai EC, Micro RNAs are complimentary to 3' UTR sequence motifs that mediate negative post-transcriptional regulation. Nature Genetics 2002;30:363-4.
Enright AJ, MicoRNA targets in Drosophila, Genome Biology 2003;5:R1.
Lewis BP, Prediction of Mammalian MicroRNA Targets, Cell 2003;115:787-98.
Stark A, Identification of Drosophila MicroRNA Targets, PLoS Biology 2003;1(3):397-409.
Lai EC, Predicting and validating microRNA targets, Genome Biology 2004;5:115.
Vella MC, Architecture of a validated microRNA::target interaction, Chemistry & Biology 2004;11:1619-23.
Brennecke J, Principles of MicroRNA-target recognition, PLoS Biology 2005;3(3):e85.
Lim LP, Microarray analysis shows that some microRNAs downregulate large numbers of target mRNAs, Nature 2005;433(7027):769-73.
Busche A, Natural killer cell-mediated rejection of experimental human lung cancer by genetic overexpression of major histocompatibility complex class I chain-related gene A, Human Gene Therapy 2006;17:135-46.
Scherr et al. Lentivirus-mediated antagomir expression for specific inhibition of miRNA function. Nucleic Acids Res. 2007;35(22):e149.
Stern-Ginossar, N. et al. Human microRNAs regulate stress-induced immune responses mediated by the receptor NKG2D. Nature Immunology, 2008;9(9):1065-73.

* cited by examiner

*Primary Examiner*—Louis Wollenberger
(74) *Attorney, Agent, or Firm*—Polsinelli Shughart PC; Teddy C. Scott, Jr.; Paul A. Jenny

(57) ABSTRACT

The present invention relates to a first group of novel bacterial and human associated oligonucleotides, here identified as Genomic Address Messenger or GAM oligonucleotide, and a second group of novel operon-like bacterial and human polynucleotides, here identified as Genomic Record or GR polynucleotide. GAM oligonucleotides selectively inhibit translation of known 'target' genes, many of which are known to be involved in various bacterial diseases. Nucleic acid molecules are provided respectively encoding 6444 GAM precursors oligonucleotides, and 726 GR polynucleotides, as are vectors and probes both comprising the nucleic acid molecules, and methods and systems for detecting GAM oligonucleotides and GR polynucleotides and specific functions and utilities thereof, for detecting expression of GAM oligonucleotides and GR polynucleotides, and for selectively enhancing and selectively inhibiting translation of the respective target genes thereof.

6 Claims, 20 Drawing Sheets

FIG. 12B

| GAM Detection Group | Published Hairpins Detection | Background Hairpins Filtering | Lab Validation of Human GAMs ||| |
| --- | --- | --- | --- | --- | --- |
| | | | Sent | Positive | % Success |
| A | 382 | ~2850000 (95 %) | 101 | 37 | 37% |
| Overall | 440 | ~3000000 | 168 | 52 | 31% |

FIG. 13B

| NUMBER | NAME | SEQUENCE (5 TO 3) | SEQUENCED | Seq ID |
|---|---|---|---|---|
| 1 | hsa-miR-21 | TAGCTTATCAGACTGATGTTGA | + | 59825 |
| 2 | hsa-miR-27b | TTCACAGTGGCTAAGTTCTGCA | + | 59826 |
| 3 | hsa-miR-186 | AAAGAATTCTCCTTTTGGGCTT | + | 59827 |
| 4 | hsa-miR-93 | AAGTGCTGTTCGTGCAGGTAGT | + | 59828 |
| 5 | hsa-miR-26a | TCAAGTAATCCAGGATAGGCTG | + | 59829 |
| 6 | hsa-miR-191 | AACGGAATCCCAAAAGCAGCTG | + | 59830 |
| 7 | hsa-miR-31 | GGCAAGATGCTGGCATAGCTGT | + | 59831 |
| 8 | hsa-miR-92 | TATTGCACTTGTCCCGGCCTGT | + | 59832 |
| 9 | GAM3418-A | ATCACATTGCCAGGGATTACCA | + | 59833 |
| 10 | GAM4426-A | GAAGTTTGAAGCCTGTTGTTCA | + | 59834 |
| 11 | GAM281-A | CACTGCACTCCAGCCTGGGCAA |   | 59835 |
| 12 | GAM7553-A | TAGGTAGTTTCCTGTTGTTGGG | + | 59836 |
| 13 | GAM5385-A | TCACAGTGAACCGGTCTCTTTC | + | 59837 |
| 14 | GAM2608-A | TAAGGTGCATCTAGTGCAGTTA |   | 59838 |
| 15 | GAM1032-A | CTAGACTGAAGCTCCTTGAGGA | + | 59839 |
| 16 | GAM3431-A | TAATACTGCCGGGTAATGATGG |   | 59840 |
| 17 | GAM7933-A | TAGCAGCACATAATGGTTTGAA |   | 59841 |
| 18 | GAM3298-A | AAAGTGCTCATAGTGCAGGTAG | + | 59842 |
| 19 | GAM7080-A | TTTCCACAGCGGCCAATTCTTC | + | 59843 |
| 20 | GAM895-A | AGCTGCCAGTTGAAGAACATTT |   | 59844 |
| 21 | GAM3770-A | AAGTTAAGAGCTCCCAGGCCTG |   | 59845 |
| 22 | GAM337162-A | ACTGCACTCCAGCCTGGGCAAC | + | 59846 |
| 23 | GAM8678-A | GTGTTCCAGGAAGTCGTCTTGA |   | 59847 |
| 24 | GAM2033-A | TCAAGCTCATTCCTCTAACCTC |   | 59848 |
| 25 | GAM7776-A | CATTGCACTCCAGCCTGGGCAA | + | 59849 |
| 26 | GAM8145-A | ACATGATCTCCTCACTCTAGGA |   | 59850 |
| 27 | GAM25-A | AATTGCTTGAACCCAGGAAGTG | + | 59851 |
| 28 | GAM7352-A | TGTTTAAGTAGCTTATTTATCT |   | 59852 |
| 29 | GAM337624-A | TCTAAGAGAAAGGAAGTTCAGA | + | 59853 |
| 30 | GAM1479-A | GAAGGCAGTAGGTTGTATAGTT | + | 59854 |
| 31 | GAM2270-A | ATCACATTGCCAGTGATTACCC | + | 59855 |
| 32 | GAM7591-A | TTGGAGTAATTCAGTATAGGTT | + | 59856 |
| 33 | GAM8285-A | AGTAGACAGTGGCAACATAGTC |   | 59857 |
| 34 | GAM6773-A | CTAGCCTGTTTGTCCTCACCCC | + | 59858 |
| 35 | GAM336818-A | TGAGGTGGGATCCCGAGGCC | + | 59859 |
| 36 | GAM336487-A | TGGCTAGGTAAGGGAAG | + | 59860 |
| 37 | GAM337620-A | AATCATCATTATTTTGAAGTTTA | + | 59861 |
| 38 | GAM336809-A | T AAGGCATTTTT A TGGT | + | 59862 |
| 39 | GAM5346-A | GCTGTTGTTAAGGGCACTTGGG |   | 59863 |
| 40 | GAM8554-A | TTCATGGGAGCAGGTGGTACAG |   | 59864 |
| 41 | GAM2701-A | ACTGCACTCCAGTCTGGGTGAC |   | 59865 |
| 42 | GAM7957-A | TCACTGCAACCTCTGCCTCCCG |   | 59866 |
| 43 | GAM391-A | CAGATCACATCCATCCGTCACC |   | 59867 |
| 44 | GAM6633-A | GCACTCAAGCCTGGGTTACAGA |   | 59868 |
| 45 | GAM19 | AGAGAGTGGCAGGTCTGTTCCT |   | 59869 |
| 46 | GAM8358-A | GATGAGGCAGCACTTGGG |   | 59870 |
| 47 | GAM3229-A | TGAGGTGGGAGAATTGCTTGAA |   | 59871 |
| 48 | GAM7052-A | CATGTAATCCCAGCTACTCAGG |   | 59872 |
| 49 | GAM3027-A (mmu-MIR-29c) | TAGCACCATTTGAAATCGGTTA | + | 59873 |
| 50 | GAM21 (mmu-MIR-130b) | CAGTGCAATGATGAAAGGGCAT | + | 59874 |
| 51 | GAM oligonucleotide (mmu-MIR 30e) | TGTAAACATCCTTGACTGGAAG | + | 59875 |

FIG. 15A

EST72223 (705 nt.)

EST72223 sequence:

CCCTTATTAGAGGATTCTGCTCATGCCAGGG<u>TGAGGTAGTAAGTTGTATTG</u>
<u>TT</u>GTGGGGTAGGGATATTAGGCCCCAATTAGAAGATAACTATACAACT  MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG  GAM25
GCTTCAGTGAGCTGAGAACACGCCACTGCACTCCAGTCCTGGGCAAC
AGAGCAAGACTCTGTCTCAGGAAAAAAAAAG

FIG. 15B

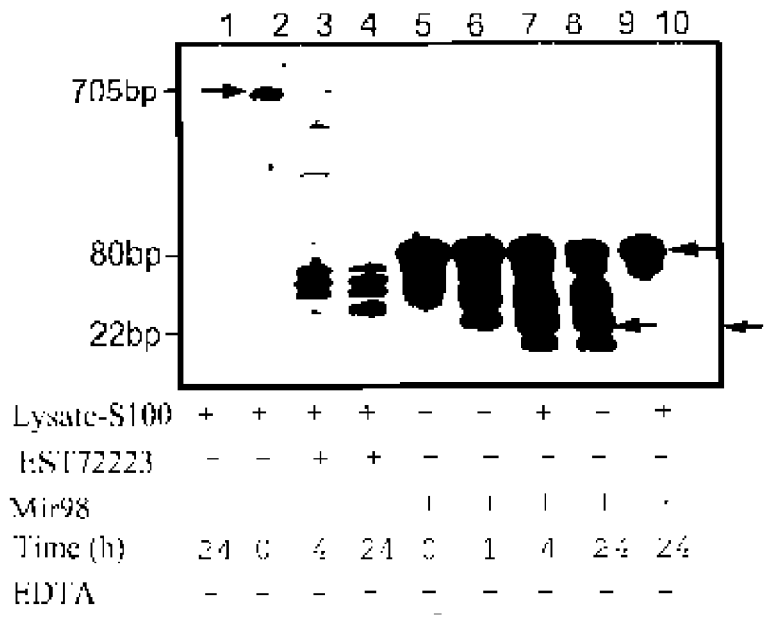

BIOINFORMATICALLY DETECTABLE GROUP OF NOVEL REGULATORY BACTERIAL AND BACTERIAL ASSOCIATED OLIGONUCLEOTIDES AND USES THEREOF

REFERENCES CITED

Altschul, S. F., Gish, W., Miller, W., Myers, E. W., and Lipman, D. J. (1990). Basic local alignment search tool. J. Mol. Biol. 215, 403-410.

Ambros, V., Lee, R. C., Lavanway, A., Williams, P. T., and Jewell, D. (2003). MicroRNAs and Other Tiny Endogenous RNAs in C. elegans 1. Curr. Biol. 13, 807-818.

Dan Gusfield, Algorithms on strings, trees, and sequences: computer science and computational biology, Cambridge University Press, 1997.

Elbashir, S. M., Lendeckel, W., and Tuschl, T. (2001). RNA interference is mediated by 21- and 22-nucleotide RNAs. Genes Dev. 15, 188-200.

Gibbs, W. W. (2003). The unseen genome: gems among the junk. Sci. Am. 289, 46-53.

Gussow, D. and Clackson, T. (1989). Direct clone characterization from plaques and colonies by the polymerase chain reaction. Nucleic Acids Res. 17, 4000.

Hamosh A, Scott A F, Amberger J, Bocchini C, Valle D and McKusick V A. (2002). Online Mendelian Inheritance in Man (OMIM), a knowledgebase of human genes and genetic disorders. Nucleic Acids Res. 30: 52-55.

Jenuth, J. P. (2000). The NCBI. Publicly available tools and resources on the Web. Methods Mol. Biol. 132, 301-312.

Kirkness, E. F. and Kerlavage, A. R. (1997). The TIGR human cDNA database. Methods Mol. Biol. 69, 261-268.

Lagos-Quintana, M., Rauhut, R., Lendeckel, W., and Tuschl, T. (2001). Identification of novel genes coding for small expressed RNAs. Science 294, 853-858.

Lau, N. C., Lim, L. P., Weinstein, E. G., and Bartel, D. P. (2001). An abundant class of tiny RNAs with probable regulatory roles in Caenorhabditis elegans. Science 294, 858-862.

Lau, N. C. and Bartel, D. P. (2003). Censors of the genome. Sci. Am. 289, 34-41.

Lim, L. P., Glasner, M. E., Yekta, S., Burge, C. B., and Bartel, D. P. (2003). Vertebrate microRNA genes. Science 299, 1540.

Mathews, D. H., Sabina, J., Zuker, M., and Turner, D. H. (1999). Expanded sequence dependence of thermodynamic parameters improves prediction of RNA secondary structure. J. Mol. Biol. 288, 911-940.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in Caenorhabditis elegans. Nature 403, 901-906.

Southern, E. M. (1992). Detection of specific sequences among DNA fragments separated by gel electrophoresis. 1975. Biotechnology 24, 122-139.

Tom M. Mitchell, Machine Learning, McGraw Hill, 1997.

Wightman, B., Ha, I., and Ruvkun, G. (1993). Posttranscriptional regulation of the heterochronic gene lin-14 by lin-4 mediates temporal pattern formation in C. elegans. Cell 75, 855-862.

Zhang, H., Kolb, F. A., Brondani, V., Billy, E., and Filipowicz, W. (2002). Human Dicer preferentially cleaves dsRNAs at their termini without a requirement for ATP. EMBO J. 21, 5875-5885.

Zuker, M. (2003). M fold web server for nucleic acid folding and hybridization prediction. Nucleic Acids Res. 31, 3406-3415.

BACKGROUND OF THE INVENTION

1. Field of the Invention

The present invention relates to a group of bioinformatically detectable novel bacterial oligonucleotides and to a group of bioinformatically detectable novel human oligonucleotides associated with bacterial infections, both are identified here as Genomic Address Messenger or GAM oligonucleotides.

All of which are believed to be related to the micro RNA (miRNA) group of oligonucleotides.

2. Description of Prior Art

Micro RNAs (miRNA), are short ~22 nt non-coding regulatory RNA oligonucleotides, found in a wide range of species, believed to function as specific gene translation repressors, sometimes involved in cell-differentiation.

The ability to detect novel miRNAs is limited by the methodologies used to detect such oligonucleotides. All miRNAs identified so far either present a visibly discernable whole body phenotype, as do Lin-4 and Let-7 (Wightman, B., Ha, I., and Ruvkun, G., Cell 75:855-862 (1993); Reinhart et al. Nature 403: 901-906 (2000)), or produce sufficient quantities of RNA so as to be detected by the standard molecular biological techniques.

Studies reporting miRNAs (Lau et al., Science 294:858-862 (2001), Lagos-Quintana et al., Science 294: 853-858 (2001)) discovered 93 miRNAs in several species, by sequencing a limited number of clones (300 by Lau and 100 by Lagos-Quintana) of small segments (i.e. size fractionated) RNA. miRNAs detected in these studies therefore, represent the more prevalent among the miRNA oligonucleotide family, and can not be much rarer than 1% of all small ~20 nt-long RNA oligonucleotides.

The aforesaid studies provide no basis for detection of miRNA oligonucleotides which either do not present a visually discernable whole body phenotype, or are rare (e.g. rarer than 0.1% of all size fractionated ~20 nt-long RNA segments expressed in the tissues examined), and therefore do not produce significant enough quantities of RNA so as to be detected by standard biological techniques. To date, miRNAs have not been detected in bacteria.

The following U.S. patents relate to bioinformatic detection of genes: U.S. Pat. No. 348,935, entitled "Statistical algorithms for folding and target accessibility prediction and design of nucleic acids", U.S. Pat. No. 6,369,195, entitled "Prostate-specific gene for diagnosis, prognosis and management of prostate cancer", and U.S. Pat. No. 6,291,666 entitled "Spike tissue-specific promoter", each of which is hereby incorporated by reference herein.

BRIEF DESCRIPTION OF SEQUENCE LISTING, LARGE TABLES AND COMPUTER PROGRAM LISTING

A sequence listing is attached to the present invention, comprising 59824 genomic sequences, is contained in a file named SEQ_LIST.txt (9477 KB, 01-Apr-04), and is hereby incorporated by reference herein.

Large tables relating to genomic sequences are attached to the present application, appear in 10 table files (size, creation date), incorporated herein: TABLE1.txt (1824 KB, 01-Apr-04); TABLE2.txt (70377 KB, 01-Apr-04); TABLE3.txt (733 KB, 01-Apr-04); TABLE4.txt (3621 KB, 01-Apr-04), TABLE5.txt (660 KB, 01-Apr-04), TABLE6.txt (3556 KB, 01-Apr-04) and TABLE7.txt (8434 KB, 01-Apr-04), TABLE8.txt (23003 KB, 01-Apr-04), TABLE9.txt (29018 KB, 01-Apr-04) and TABLE10.txt (5265 KB, 01-Apr-04), all of which are incorporated by reference herein.

LENGTHY TABLES

The patent contains a lengthy table section. A copy of the table is available in electronic form from the USPTO web site (http://seqdata.uspto.gov/?pageRequest=docDetail&DocID=US07842800B2). An electronic copy of the table will also be available from the USPTO upon request and payment of the fee set forth in 37 CFR 1.19(b)(3).

A computer program listing of a computer program constructed and operative in accordance with a preferred embodiment of the present invention is enclosed on an electronic medium in computer readable form, and is hereby incorporated by reference herein. The computer program listing is contained in 6 files, the name, sizes and creation date of which are as follows: AUXILARY_FILES.txt (117K, 14-Nov-03); EDIT_DISTANCE.txt (144K, 24-Nov-03); FIRST-K.txt (96K, 24-Nov-03); HAIRPIN_PREDICTION.txt (19K, 25-Mar-04); TWO_PHASED_SIDE_SELECTOR.txt (4K, 14-Nov-03); and TWO_PHASED_PREDICTOR.txt (74K, 14-Nov-03).

SUMMARY OF THE INVENTION

The present invention relates to an isolated nucleic acid selected from the group consisting of (a) SEQ ID NO: 55663, (b) a DNA encoding the nucleic acid of (a), wherein the DNA is identical in length to (a); and (c) the complement of (a) or (b), wherein the complement is identical in length to the nucleic acid of (a) or (b). Additionally, the present invention relates to vectors or probes comprising a human insert, wherein the human insert consists of the nucleic acid selected from the group consisting of (a) SEQ ID NO: 55663, (b) a DNA encoding the nucleic acid of (a), wherein the DNA is identical in length to (a); and (c) the complement of (a) or (b), wherein the complement is identical in length to the nucleic acid of (a) or (b), and wherein the vector or probe comprises no other insert but the nucleic acid as described above.

The present invention also relates to an isolated nucleic acid selected from the group consisting of (a) SEQ ID NO: 1485, (b) a DNA encoding the nucleic acid of (a), wherein the DNA is identical in length to (a); and (c) the complement of (a) or (b), wherein the complement is identical in length to the nucleic acid of (a) or (b). Additionally, the present invention relates to vectors or probes comprising a human insert, wherein the human insert consists of the nucleic acid selected from the group consisting of (a) SEQ ID NO: 1485, (b) a DNA encoding the nucleic acid of (a), wherein the DNA is identical in length to (a); and (c) the complement of (a) or (b), wherein the complement is identical in length to the nucleic acid of (a) or (b), and wherein the vector or probe comprises no other insert but the nucleic acid as described above.

BRIEF DESCRIPTION OF DRAWINGS

FIG. 12B is a table summarizing laboratory validation results which validate efficacy of a bioinformatic oligonucleotide detection system constructed and operative in accordance with a preferred embodiment of the present invention;

FIG. 13A and FIG. 13B are a picture and a summary table of laboratory results validating the expression of novel human oligonucleotides detected by a bioinformatic oligonucleotide detection engine constructed and operative in accordance with a preferred embodiment of the present invention, thereby validating the efficacy of the oligonucleotide detection engine of the present invention;

FIG. 15A is an annotated sequence of EST72223 (SEQ ID NO: 59887) comprising known human miRNA oligonucleotide MIR98 and novel human oligonucleotide GAM25 PRECURSOR detected by the oligonucleotide detection system of the present invention; and FIGS. 15B, 15C and 15D are pictures of laboratory results demonstrating laboratory confirmation of expression of known human oligonucleotide MIR98 and of novel bioinformatically detected human GAM25 RNA respectively, both of FIG. 15A, thus validating the bioinformatic oligonucleotide detection system of the present invention;

BRIEF DESCRIPTION OF SEQUENCES

Figure 1:
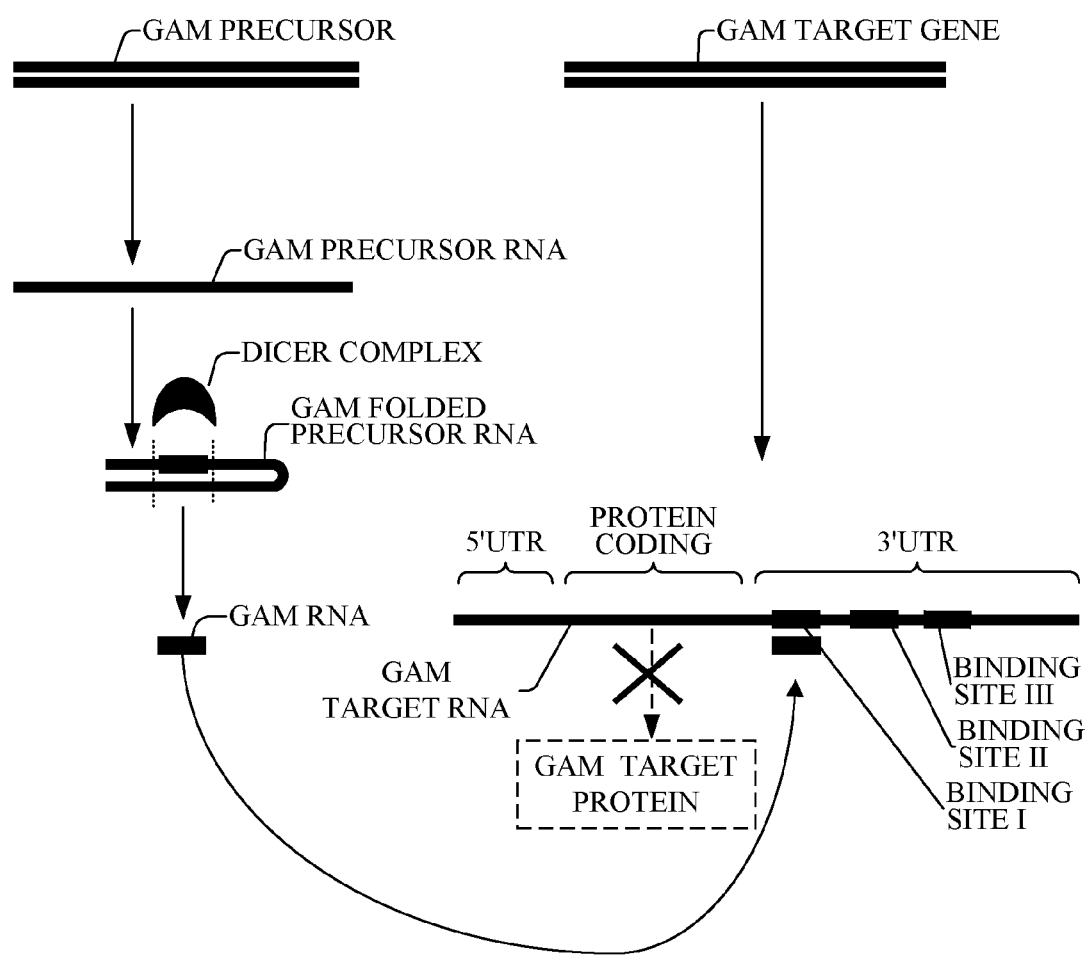
FIG. 1 is a simplified diagram illustrating a mode by which oligonucleotide of a novel group of oligonucleotides of the present invention modulates expression of known target genes.

A Sequence Listing of genomic sequences of the present invention designated SEQ ID NO:1 through SEQ ID: 59824 is attached to this application, and is hereby incorporated herein. The genomic listing comprises the following nucleotide sequences: nucleotide sequences of 6444 GAM precursors of respective novel oligonucleotides of the present invention; nucleotide sequences of 6456 GAM RNA oligonucleotides of respective novel oligonucleotides of the present invention; and nucleotide sequences of 13640 target gene binding sites of respective novel oligonucleotides of the present invention.

DETAILED DESCRIPTION

The present invention relates to a novel group of bioinformatically detectable bacterial regulatory RNA oligonucleotides, which repress expression of human target genes, by means of complementary hybridization to binding sites in untranslated regions of these target genes. It is believed that this novel group of bacterial oligonucleotides represents a pervasive bacterial mechanism of attacking a host, and therefore knowledge of this novel group of bacterial oligonucleotides may be useful in preventing and treating bacterial diseases.

Additionally, the present invention relates to a novel group of bioinformatically detectable human regulatory RNA oligonucleotides, which repress expression of human target genes associated with the bacterial infection, by means of complementary hybridization to binding sites in untranslated regions of these target genes. It is believed that this novel group of human oligonucleotides represents a pervasive novel host response mechanism, and therefore knowledge of this novel group of human oligonucleotides may be useful in preventing and treating bacterial diseases. In various preferred embodiments, the present invention seeks to provide improved method and system for detection and prevention of bacterial diseases, which are mediated by this group of novel oligonucleotides.

Accordingly, the invention provides several substantially pure nucleic acids (e.g., genomic DNA, cDNA or synthetic DNA) each comprising a novel GAM oligonucleotide, vectors comprising the DNAs, probes comprising the DNAs, a method and system for selectively modulating translation of known human target genes utilizing the vectors, and a method and system utilizing the CAM probes to modulate expression of human target genes.

The present invention represents a scientific breakthrough, disclosing novel miRNA-like oligonucleotides the number of which is dramatically larger than previously believed existed. Prior-art studies reporting miRNAs ((Lau et al., Science 294358-862 (2001), Lagos-Quintana et al., Science 294: 853-858 (2001)) discovered 93 miRNAs in several species, including 21 in human, using conventional molecular biology methods, such as cloning and sequencing.

Molecular biology methodologies employed by these studies are limited in their ability to detect rare miRNA oligonucleotides, since these studies relied on sequencing of a limited number of clones (300 clones by Lau and 100 clones by Lagos-Quintana) of small segments (i.e. size fractionated) of RNA. MicroRNAs detected in these studies therefore, represent the more prevalent among the miRNA oligonucleotide family, and are typically not be much rarer than 1% of all small -20 nt-long RNA oligonucleotides present in the tissue from the RNA was extracted. Recent studies state the number of miRNA oligonucleotides to be limited, and describe the limited sensitivity of available methods for detection of miRNA: The estimate of 255 human miRNA oligonucleotides is an upper bound implying that no more than 40 miRNA oligonucleotides remain to be identified in mammals (Lim et al., Science, 299:1540 (2003)); Estimates place the total number of vertebrate miRNA genes at about 200-250 (Ambros et al. Curr. Biol. 13307-818 (2003)); and Confirmation of very low abundance miRNAs awaits the application of detection methods more sensitive than Northern blots (Ambros et al. Curr. Biol. 13307-818 (2003)).

The oligonucleotides of the present invention represent a revolutionary new dimension of genomics and of biology: a dimension comprising a huge number of non-protein coding oligonucleotides which modulate expression of thousands of proteins and are associated with numerous major diseases. This new dimension disclosed by the present invention dismantles a central dogma that has dominated life-sciences during the past 50 years, a dogma which has emphasized the importance of protein coding regions of the genome, holding non-protein coding regions to be of little consequence, often dubbing them junk DNA.

Indeed, only in November, 2003 has this long held belief as to the low importance of non-protein coding regions been vocally challenged. As an example, an article titled The Unseen Genome -Gems in the Junk (Gibbs, W.W. Sci. Am. 289:46-53 (2003)) asserts that the failure to recognize the importance of non-protein- coding regions may well go down as one of the biggest mistakes in the history of molecular biology. Gibbs further asserts that what was considered junk because it was not understood, may in fact turn out to be the very basis of human complexity. The present invention provides a dramatic leap in understanding specific important roles of non-protein coding regions.

An additional scientific breakthrough of the present invention is a novel conceptual model disclosed by the present invention, which conceptual model is preferably used to encode in a genome the determination of cell differentiation, utilizing oligonucleotides and polynucleotides of the present invention.

In various preferred embodiments, the present invention seeks to provide an improved method and system for specific modulation of the expression of specific target genes involved in significant human diseases. It also provides an improved method and system for detection of the expression of novel oligonucleotides of the present invention, which modulate these target genes. In many cases the target genes may be known and fully characterized, however in alternative embodiments of the present invention, unknown or less well characterized genes may be targeted.

A Nucleic acid is defined as a ribonucleic acid (RNA) molecule, or a deoxyribonucleic acid (DNA) molecule, or complementary deoxyribonucleic acid (cDNA), comprising either naturally occurring nucleotides or non-naturally occurring nucleotides. Substantially pure nucleic acid, Isolated Nucleic Acid, Isolated Oligoucleotide and Isolated Polynucleotide are defined as a nucleic acid that is free of the genome of the organism from which the nucleic acid is derived, and include, for example, a recombinant nucleic acid which is incorporated into a vector, into an autonomously replicating plasmid or virus, or into the genomic nucleic acid of a prokaryote or eukaryote at a site other than its natural site; or which exists as a separate molecule (e.g., a cDNA or a genomic or cDNA fragment produced by PCR or restriction endonuclease digestion) independent of other nucleic acids. An Oligonucleotide is defined as a nucleic acid comprising 2-139 nucleotides, or preferably 16-120 nucleotides. A Polynucleotide is defined as a nucleic acid comprising 140-5000 nucleotides, or preferably 140-1000 nucleotides.

A Complementary sequence is defined as a first nucleotide sequence which reverses complementary of a second nucleotide sequence: the first nucleotide sequence is reversed relative to a second nucleotide sequence, and wherein each nucleotide in the first nucleotide sequence is complementary to a corresponding nucleotide in the second nucleotide sequence (e.g. ATGGC is the complementary sequence of GCCAT).

Hybridization, Binding and Annealing are defined as hybridization, under in-vivo physiologic conditions, of a first nucleic acid to a second nucleic acid, which second nucleic acid is at least partially complementary to the first nucleic acid. A Hairpin Structure is defined as an oligonucleotide having a nucleotide sequence that is 50-140 nucleotides in length, the first half of which nucleotide sequence is at least partially complementary to the second part thereof, thereby causing the nucleic acid to fold onto itself, forming a secondary hairpin structure.

A Hairpin Shaped Precursor is defined as a Hairpin Structure which is processed by a Dicer enzyme complex, yielding an oligonucleotide which is about 19 to about 24 nucleotides in length. "Inhibiting translation" is defined as the ability to prevent synthesis of a specific protein encoded by a respective gene by means of inhibiting the translation of the mRNA of this gene. For example, inhibiting translation may include the following steps: (1) a DNA segment encodes an RNA, the first half of whose sequence is partially complementary to the second half thereof; (2) the precursor folds onto itself forming a hairpin-shaped precursor; (3) a Dicer enzyme complex cuts the hairpin shaped precursor yielding an oligonucleotide that is approximately 22 nt in length; (4) the oligonucleotide binds complementarily to at least one binding site, having a nucleotide sequence that is at least partially complentary to the oligonucleotide, which binding site is located in the mRNA of a target gene, preferably in the untranslated region (UTR) of a target gene, such that the binding inhibits translation of the target protein.

A "Translation inhibitor site" is defined as the minimal nucleotide sequence sufficient to inhibit translation.

There is thus provided in accordance with a preferred embodiment of the present invention a bioinformatically detectable isolated oligonucleotide which is endogenously processed from a hairpin-shaped precursor, and anneals to a portion of a mRNA transcript of a target gene, wherein binding of the oligonucleotide to the mRNA transcript represses expression of the target gene, and wherein the oligonucleotide has at least 80% sequence identity with a nucleotide sequence selected from the group consisting of SEQ ID NOS: 1-6456.

There is further provided in accordance with another preferred embodiment of the present invention a bioinformatically detectable isolated oligonucleotide having a nucleotide sequence selected from the group consisting of SEQ ID NOS: 1-6456.

There is still further provided in accordance with another preferred embodiment of the present invention a bioinformatically detectable first oligonucleotide which is a portion of a mRNA transcript of a target gene, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOS: 1-6456.

There is additionally provided in accordance with another preferred embodiment of the present invention a bioinformatically detectable oligonucleotide having a nucleotide sequence selected from the group consisting of SEQ ID NOS: 1-6456.

There is moreover provided in accordance with another preferred embodiment of the present invention a bioinformatically detectable isolated oligonucleotide which anneals to a portion of a mRNA transcript of a target gene associated with *Escherichia coli* CFT073 infection, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOS: 6 and 7044-8222, and (b) the complement of a sequence selected from the group consisting of SEQ ID NOS: 19991 and 18424-2 1435.

There is further provided in accordance with another preferred embodiment of the present invention a bioinformatically detectable first oligonucleotide which is a portion of a mRNA transcript of a target gene associated with Escherichia coli CFT073, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOS: 6 and 7044-8222.

There is still further provided in accordance with another preferred embodiment of the present invention a bioinformatically detectable isolated oligonucleotide which anneals to a portion of a mRNA transcript of a target gene associated with Mycobacterium avium subsp. paratuberculosis infection, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOS: 1, 2, 3, 4, 5 and 8468-10252, and (b) the complement of a sequence selected from the group consisting of SEQ ID NOS: 24070, 24503, 24604, 24799, 24951 and 21948-25640.

There is additionally provided in accordance with another preferred embodiment of the present invention a bioinformatically detectable first oligonucleotide which is a portion of a mRNA transcript of a target gene associated with Mycobacterium avium subsp. paratuberculosis, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOS: 1, 2, 3, 4, 5 and 8468-10252.

There is moreover provided in accordance with another preferred embodiment of the present invention a bioinformatically detectable isolated oligonucleotide which anneals to a portion of a mRNA transcript of a target gene associated with *Mycobacterium bovis* subsp *bovis* AF2122197 infection, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOS: 1, 2, 3, 4, 5 and 10253-11953, and (b) the complement of a sequence selected from the group consisting of SEQ ID NOS: 26741, 27115, 27315, 27443, 27664, 28350 and 25641-29147.

There is further provided in accordance with another preferred embodiment of the present invention a bioinformatically detectable first oligonucleotide which is a portion of a mRNA transcript of a target gene associated with *Mycobacterium bovis* subsp *bovis*AF2122197, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOS: 1, 2, 3, 4, 5 and 10253-11953.

There is still further provided in accordance with another preferred embodiment of the present invention a bioinformatically detectable isolated oligonucleotide which anneals to a portion of a mRNA transcript of a target gene associated with *Mycobacterium tuberculosis* CDC15 5 1 infection, wherein binding of the oligonucleotide to the mRNA transcript represses expression of the target gene, and wherein the oligonucleotide has at least 80% sequence identity with a nucleotide sequence selected from the group consisting of: (a) a sequence selected from the group consisting of SEQ ID NOS:1, 2, 3, 4, 5 and 12752-14275, and (b) the complement of a sequence selected from the group consisting of SEQ ID NOS: 32492, 33020, 33133, 33366, 33675 and 30886-33928.

There is additionally provided in accordance with another preferred embodiment of the present invention a bioinformatically detectable first oligonucleotide which is a portion of a mRNA transcript of a target gene associated with *Mycobacterium tuberculosis* CDC15 51, and anneals to a second oligonucleotide that is endogenously processed from a hairpin precursor, wherein binding of the first oligonucleotide to the second oligonucleotide represses expression of the target gene, and wherein nucleotide sequence of the second nucleotide is selected from the group consisting of SEQ ID NOS: 1, 2, 3, 4, 5 and 12752-14275.

There is moreover provided in accordance with another preferred embodiment of the present invention a method for bioinformatic detection of microRNA oligonucleotides, the method including: bioinformatically detecting a hairpin shaped precursor oligonucleotide, bioinformatically detecting an oligonucleotide which is endogenously processed from the hairpin shaped precursor oligonucleotide, and bioinformatically detecting a target gene of the oligonucleotide wherein the oligonucleotide anneals to at least one portion of a mRNA transcript of the target gene, and wherein the binding represses expression of the target gene, and the target gene is associated with a disease.

Reference is now made to FIG. 1, which is a simplified diagram describing a plurality of novel bioinformatically detected oligonucleotide of the present invention referred to here as Genomic Address Messenger (GAM) oligonucleotide, which modulates expression of respective target genes whose function and utility is known in the art.

GAM is a novel bioinformatically detectable regulatory, non protein coding, microRNA (miRNA)-like oligonucleotide. The method by which GAM is detected is described with additional reference to FIGS. 1-8.

GAM PRECURSOR is preferably encoded by a bacterial genome. Alternatively or additionally GAM PRECURSOR is preferably encoded by the human genome. GAM TARGET GENE is a gene encoded by the human genome.

GAM PRECURSOR encodes a GAM PRECURSOR RNA. Similar to other miRNA oligonucleotides GAM PRECURSOR RNA does not encode a protein.

GAM PRECURSOR RNA folds onto itself, forming GAM FOLDED PRECURSOR RNA which has a two-dimensional 'hairpin structure'. As is well known in the art, this 'hairpin structure', is typical of RNA encoded by known miRNA oligonucleotides, and is due to the fact that the nucleotide sequence of the first half of the RNA encoded by a miRNA oligonucleotide is a fully or partially complementary sequence of the nucleotide sequence of the second half thereof. By complementary is meant a sequence which is reversed and wherein each nucleotide is replaced by a complementary nucleotide, as is well known in the art (e.g. ATGGC is the complementary sequence of GCCAT). An enzyme complex designated DICER COMPLEX, 'dices' the GAM FOLDED PRECURSOR RNA yielding a GAM RNA in the form of a single stranded ~22 nt long RNA segment. As is known in the art, 'dicing' of a hairpin structured RNA precursor product to yield a short ~22 nt RNA segment is catalyzed by an enzyme complex Dicer RNaseIII together with other necessary proteins.

GAM TARGET GENE encodes a corresponding messenger RNA, GAM TARGET RNA. Each of the GAM TARGET RNAs of the present invention comprises three regions, as is typical of mRNA of a protein coding gene: a 5 untranslated region, a protein coding region and a 3' untranslated region, designated 5'UTR, PROTEIN CODING and 3'UTR respectively.

GAM RNA binds complementarily to one or more target binding sites located in untranslated regions of each of the GAM TARGET RNAs of the present invention. This complementary binding is due to the fact that the nucleotide sequence of GAM RNA is a partial or fully complementary sequence of the nucleotide sequence of each of the target binding sites. As an illustration, FIG. 1 shows three such target binding sites, designated BINDING SITE I, BINDING SITE II and BINDING SITE III respectively. It is appreciated that the number of target binding sites shown in FIG. 1 is only illustrative and that any suitable number of target binding sites may be present. It is further appreciated that although FIG. 1 shows target binding sites only in the 3'UTR region these target binding sites may be located instead in the 5'UTR region or in both 3'UTR and 5'UTR regions.

The complementary binding of GAM RNA to target binding sites on GAM TARGET RNA, such as BINDING SITE I, BINDING SITE II and BINDING SITE III, inhibits translation of each of the GAM TARGET RNAs of the present invention into GAM TARGET PROTEIN, which is shown surrounded by a broken line.

It is appreciated that GAM TARGET GENE in fact represents a plurality of GAM target genes. The mRNA of each one of this plurality of GAM target genes comprises one or more target binding sites, each having a nucleotide sequence which is at least partly complementary to GAM RNA and which when bound by GAM RNA causes inhibition of translation of the GAM target mRNA into a corresponding GAM target protein.

The mechanism of the translational inhibition exerted by GAM RNA on one or more GAM TARGET GENEs may be similar or identical to the known mechanism of translational inhibition exerted by known miRNA oligonucleotides.

The nucleotide sequences of each of a plurality of GAM oligonucleotides described by FIG. 1 and their respective genomic sources and genomic locations are set forth in Tables 1-3, hereby incorporated herein. Specifically, in Table 1, line 3060, 20697, 24356 and 28626 describes GAM RNA (miRNA) as set forth in SEQ ID NOs:1485, 9423, 10931, 12760 respectively is shown as predicted from human.

| GAM SEQ-ID | GAM NAME | GAM RNA SEQUENCE | GAM ORGANISM | GAM POS |
|---|---|---|---|---|
| 1485 | GAM338499 | AAAGTGCTTCTCTTTGGTGGGT | Human | A |
| 9423 | GAM338499 | AAAGTGCTTCTCTTTGGTGGGT | Human | A |
| 10931 | GAM338499 | AAAGTGCTTCTCTTTGGTGGGT | Human | A |
| 12760 | GAM338499 | AAAGTGCTTCTCTTTGGTGGGT | Human | A |

In Table 2, lines 227057-227161, describes GAM PRECURSOR RNA (hairpin) as set forth in SEQ ID NO: 55663 and as it relates to FIGS. 1-8.

| GAM NAME | GAM ORGANISM | PRECUR SEQ-ID | PRECURSOR SEQUENCE | GAM DESCRIPTION |
|---|---|---|---|---|
| GAM 338499 | Human | 55663 | TCTCAAGCTG TGAGTCTACA AAGGGAAGCC CTTTCTGTTG CTTTCTGTTG TCTAAAAGAA AAGAAAGTGC TTCTCTTTGG TGGGTTACGG TTTGAGA | FIG. 1 further provides a conceptual description of another novel bioinformatically detected human oligonucleotide of the present invention referred to here as Genomic Address Messenger 338499 (GAM338499) oligonucleotide, which modulates expression of respective target genes whose function and utility is known in the art. GAM338499 is a novel bioinformatically detectable regulatory, non protein coding, microRNA (miRNA)-like oligonucleotide. The method by which GAM338499 is detected is described with additional reference to FIGS. 1-8. GAM338499 precursor, herein designated GAM PRECURSOR, is encoded by the Human genome. GAM338499 target gene, herein designated GAM TARGET GENE, is a target gene encoded by the human genome. GAM338499 precursor, herein designated GAM PRECURSOR, encodes a GAM338499 precursor RNA, herein designated GAM PRECURSOR RNA. Similar to other miRNA oligonucleotides GAM338499 precursor RNA does not encode a protein. GAM338499 precursor RNA Folds onto itself, forming GAM338499 folded precursor RNA, Herein designated GAM FOLDED PRECURSOR RNA, which has a two-dimensional 'hairpin structure'. As is well known in the art, this 'hairpin structure', is typical of RNA encoded by known miRNA oligonucleotides, and is due to the fact that the nucleotide sequence of first half of the RNA encodedby a miRNA oligonucleotide is a fully or partially complementary sequence of the nucleotide sequence of the second half thereof. A nucleotide sequence identical or highly similar to the nucleotide sequence of GAM338499 precursor RNA is designated SEQ ID NO: 55663, and is provided hereinbelow with reference to the sequence listing part. Nucleotide sequence SEQ ID NO: 55663 is located from position 58915162 to position 58915248 relative to chromosome 19 on the '+' strand. A schematic representation of a predicted secondary folding of GAM338499 folded precursor RNA, herein designated GAM FOLDED PRECURSOR RNA, is set forth in Table 4 incorporated herein. An enzyme complex designated DICER COMPLEX, 'dices' the GAM338499 |

| GAM NAME | GAM ORGANISM | PRECUR SEQ-ID | PRECURSOR SEQUENCE | GAM DESCRIPTION |
|---|---|---|---|---|
| | | | | folded precursor RNA yielding a GAM338499 RNA, herein designated GAM RNA, in the form of a single stranded ~22nt long RNA segment. As is known in the art, 'dicing' of a hairpin structured RNA precursor product to yield a short ~22nt RNA segment is catalyzed by an enzyme complex Dicer RNaseIII together with other necessary proteins. Table 5 provides a nucleotide sequence that is highly likely to be identical or highly similar to the nucleotide sequence of GAM338499 RNA, hereby incorporated herein. GAM338499 target gene, herein designated GAM TARGET GENE, encodes a corresponding messenger RNA, GAM338499 target RNA, herein designated TARGET RNA. GAM338499 target RNA comprises three regions, as is typical of mRNA of a protein coding gene: a 5' untranslated region, a protein coding region and a 3' untranslated region, designated 5'UTR, PROTEIN CODING and 3'UTR respectively. GAM338499 RNA, herein designated GAM RNA, binds complementarily to one or more target binding sites located in untranslated regions of GAM338499 target RNA. This complementary binding is due to the fact that the nucleotide sequence of GAM338499 RNA is a partial or fully complementary sequence of the nucleotide sequence of each of the target binding sites. As an illustration, FIG. 1 shows three such target binding sites, designated BINDING SITE I, BINDING SITE II and BINDING SITE III respectively. It is appreciated that the number of target binding sites shown in FIG. 1 is only illustrative and that any suitable number of target binding sites may be present. It is further appreciated that although FIG. 1 shows target binding sites only in the 3'UTR region these target binding sites may be located instead in the 5'UTR region or in both 3'UTR and 5'UTR regions The complementary binding of GAM338499 RNA, herein designated GAM RNA, to target binding sites on GAM338499 target RNA, herein designated GAM TARGET RNA, such as BINDING SITE I, BINDING SITE II and BINDING SITE III, inhibits translation of GAM338499 target RNA into GAM338499 target protein, herein designated GAM TARGET PROTEIN, which is shown surrounded by a broken line. It is appreciated that GAM338499 target gene, herein designated GAM TARGET GENE, in fact represents a plurality of GAM338499 target genes. The mRNA of each one of this plurality of GAM338499 target genes comprises one or more target binding sites, each having a nucleotide sequence which is at least partly complementary to GAM338499 RNA, herein designated GAM RNA, and which when bound by GAM338499 RNA causes inhibition of translation of the GAM338499 target mRNA into a corresponding GAM338499 target protein. The mechanism of the translational inhibition exerted by GAM338499 RNA, herein designated GAM RNA, on one or more GAM338499 target genes, herein collectively designated GAM TARGET GENE, may be similar or identical to the known mechanism of ranslational inhibition exerted by known miRNA oligonucleotides. Nucleotide sequence of GAM338499 precursor RNA, herein designated GAM PRECURSOR RNA, its respective genomic |

-continued

| GAM NAME | GAM ORGANISM | PRECUR SEQ-ID | PRECURSOR SEQUENCE | GAM DESCRIPTION |
|---|---|---|---|---|
| | | | | source and genomic location and a schematic representation of a predicted secondary folding of GAM338499 folded precursor RNA, herein designated GAM FOLDED PRECURSOR RNA, are set forth in Tables 3-4, incorporated herein. Nucleotide sequences of a 'diced' GAM338499 RNA, herein designated GAM RNA, of GAM338499 folded precursor RNA are set forth in Table 5, incorporated herein. Nucleotide sequences of target binding sites, such as BINDING SITE-I, BINDING SITE-II and BINDING SITE-III of FIG. 1, found on GAM338499 target RNA, herein designated GAM TARGET RNA, and a schematic representation of the complementarity of each of these target binding sites to GAM338499 RNA, herein designated GAM RNA, are set forth in Tables 6-7, incorporated herein. It is appreciated that specific functions and accordingly utilities of GAM338499 RNA are correlated with and may be deduced from the identity of the GAM338499 target gene inhibited thereby, and whose functions are set forth in Table 8, incorporated herein. |

Table 3, line 4432, shows data relating to the source and location of the GAM oligonucleotide, specifically the GAM PRECRSOR (hairpin) and its position in the genomic sequence of human.

| GAM NAME | PRECUR SEQ-ID | GAM ORGANISM | SOURCE | SRC-STR AND | SRC-START OFFSET | SRC-END OFFSET |
|---|---|---|---|---|---|---|
| GAM338499 | 55663 | Human | 19 | + | 58915162 | 58915248 |

The nucleotide sequences of GAM PRECURSOR RNAs, and a schematic representation of a predicted secondary folding of GAM FOLDED PRECURSOR RNAs, of each of a plurality of GAM oligonucleotides described by FIG. 1 are set forth in Table 4, hereby incorporated herein. Table 4 lines 11968-11972, shows a schematic representation of the GAM folder precursor as set forth in SEQ ID NO:55663, beginning at the 5' end (beginning of upper row) to the 3' end (beginning of lower row), where the hairpin loop is positioned at the right part of the drawing.

The nucleotide sequences of diced GAM RNAs of each of a plurality of GAM oligonucleotides described by FIG. 1 are set forth in Table 5, hereby incorporated herein. Table 5, line 4254 shows the mature GAM RNA as set forth in SEQ ID NO: 55663 as sliced by DICER from the GAM PRECURSOR sequence (hairpin) as set forth in SEQ ID NO: 55663.

| GAM NAME | GAM ORGANISM | GAM RNA SEQUENCE | PRECUR SEQ-ID | GAM POS |
|---|---|---|---|---|
| GAM338499 | Human | AAAGTGCTTCTCTTTGGTGGGT | 55663 | A |

The Nucleotide sequences of target binding sites, such as BINDING SITE I, BINDING SITE II and BINDING SITE III found on GAM TARGET RNAs of each of a plurality of GAM oligonucleotides described by FIG. 1, and a schematic representation of the complementarity of each of these target binding sites to each of a plurality of GAM RNAs described by FIG. 1 are set forth in Tables 6-7, hereby incorporated herein. Table 6 shows data relating to the SEQ ID NO: of the

| GAM NAME | PRECUR SEQ-ID | GAM ORGANISM | PRECURSOR-SEQUENCE | GAM FOLDED PRECURSOR RNA |
|---|---|---|---|---|
| GAM 338499 | 55663 | Human | TCTCAAGCTGTGAGTCTACA TAAAA AGGGAAGCCCTTTCTGTTG TCTAAAAGAAAAGAAAGTGC TTCTCTTTGGTGGGTTACGG - ----- TTTGAGA | G    TA        C      GTTG-<br>TCTCAAGCTGTGA TC  CAAAGGGAAGC CTTTCT  TC<br>AGAGTTTGGCATT GG  GTTTCTCTTCG GAAAGA  AG<br>G    TG        T      AA- |

GAM target binding site sequence of the target gene name as bound by the GAM RNA as set forth in SEQ ID NO:1485. Table 6, lines 11966 and 13602 related to target binding site SEQ ID NO: 23420 and 24238 respectively.

| TARGET BINDING SITE | TARGET SEQ-ID | TARGET ORGANISM | TARGET | TARGET BINDING SITE SEQUENCE |
|---|---|---|---|---|
| 23420 | | Human | MICA | CACAAGCACTTT:11966 |
| 24238 | | Human | MICA | AAAAGCACTTA:13602 |

Table 7, lines 26274-26282 shows data relating to target genes and binding site of GAM oligonucleotides.

| GAM NAME | GAM ORGANISM | GAM RNA SEQUENCE | TARGET BS-SEQ | TARGET | TARGET REF-ID | TARGET ORGANISM | UTR | BINDING-SITE DRAW (UPPER:GAM;LOWER:TARGET) | GAM POS |
|---|---|---|---|---|---|---|---|---|---|
| GAM 338499 | Human | AAAGTGCT TCTCTTTG GTGGGT | AAAAGCAC TTA | MICA | NM_000247 | Human | 3 | ---- -- -----         A<br>     A  AA     AGCACTT<br>     T  TT     TCGTGAA<br>TGGG  GG TCTCT A | A |
| GAM 338499 | Human | AAAGTGCT TCTCTTTG GTGGGT | CACAAGCA CTTT | MICA | NM_000247 | Human | 3 | -- - - ------    C AC A    AGCACTTT<br>   G TG T    TCGTGAAA | A |

It is appreciated that specific functions and accordingly utilities of each of a plurality of GAM oligonucleotides described by FIG.1 are correlated with, and may be deduced from the identity of the GAM TARGET GENEs inhibited thereby, and whose functions are set forth in Table 8, hereby incorporated herein. Table 8, lines 80406-80439 shows data relating to the function and utilities of GAM RNA as set forth in SEQ ID NO: 1485.

| GAM NAME | GAM RNA SEQUENCE | GAM ORGANISM | TARGET | TARGET ORGANISM | GAM FUNCTION | GAM POS |
|---|---|---|---|---|---|---|
| GAM 338 499 | AAAGTGCT TCTCTTTG GTGGGT | Human | MICA | Human | GAM338499 is a human miRNA-like oligonucleotide, which targets MHC class I polypeptide-related sequence A (MICA, Accession NM_000247), a human target gene, as part of a Host response mechanism associated with Mycobacterium avium subsp paratuberculosis, Mycobacterium bovis subsp bovis AF2122/and Mycobacterium tuberculosis CDC1551 infections. MICA BINDING SITE1 and MICA BINDING SITE2 are human target binding sites found in untranslated regions of mRNA encoded by MICA, corresponding to target binding sites such as BINDING SITE I, BINDING SITE II or BINDING SITE III of FIG.1. Nucleotide sequences of MICA BINDING SITE1 and MICA BINDING SITE2, and secondary structure complementarity to the nucleotide sequence of GAM338499 RNA are set forth in Tables 6-7, hereby incorporated herein. A function of GAM338499 is therefore inhibition of MICA, a GAM338499 human target gene which encodes for a protien that binds to the receptors on T-cells and NK cells, activating cytolytic responses, induced by oxidative stress and bacteria. MICA is associated with Mycobacterium avium subsp paratuberculosis, Mycobacterium bovis subsp bovis AF2122/97 and Mycobacterium tuberculosis CDC1551 infections, and therefore GAM338499 is ssociated with the abovementioned infections, as part of a host response mechanism. Accordingly, utilities of GAM338499 include diagnosis, prevention and treatment of Mycobacterium avium subsp. paratuberculosis, Mycobacterium bovis subsp bovis AF2122/97 and Mycobacterium tuberculosis CDC1551 | A |

-continued

| GAM NAME | GAM RNA SEQUENCE | GAM ORGANISM | TARGET ORGANISM | GAM TARGET FUNCTION | GAM POS |
|---|---|---|---|---|---|
| | | | | infections and associated clinical conditions. The function of MICA and its association with various diseases and clinical conditions, has been established by previous studies, as described hereinabove with reference to GAM336293. | |

Studies documenting well known correlations between each of a plurality of GAM TARGET GENEs of the GAM oligonucleotides of FIG. 1, and known functions and diseases are listed in Table 9, hereby incorporated herein.

The present invention discloses a novel group of bacterial and human oligonucleotides, belonging to the miRNA-like oligonucleotides group, here termed GAM oligonucleotides, for which a specific complementary binding has been determined bioinformatically.

Figure 2:
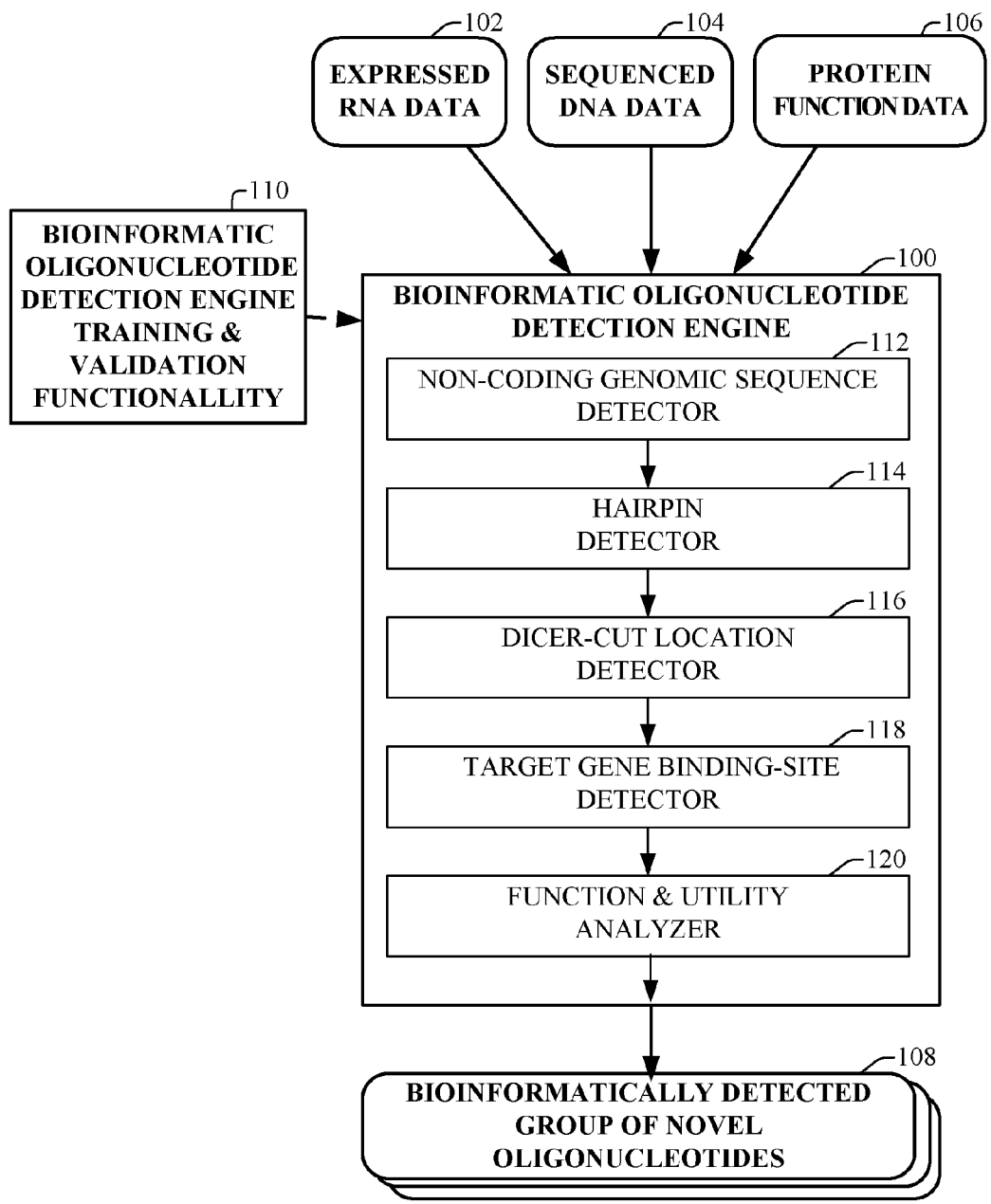
FIG. 2 is a simplified block diagram illustrating a bioinformatic oligonucleotide detection system capable of detecting oligonucleotides of the novel group of oligonucleotides of the present invention, which system is constructed and operative in accordance with a preferred embodiment of the present invention.

Reference is now made to FIG. 2 which is a simplified block diagram illustrating a bioinformatic oligonucleotide detection system and method constructed and operative in accordance with a preferred embodiment of the present invention.

An important feature of the present invention is a BIOINFORMATIC OLIGONUCLEOTIDE DETECTION ENGINE 100, which is capable of bioinformatically detecting oligonucleotides of the present invention.

The functionality of the BIOINFORMATIC OLIGONUCLEOTIDE DETECTION ENGINE 100 includes receiving EXPRESSED RNA DATA 102, SEQUENCED DNA DATA 104, and PROTEIN FUNCTION DATA 106; performing a complex process of analysis of this data as elaborated hereinbelow, and based on this analysis provides information, designated by reference numeral 108, identifying and describing features of novel oligonucleotides.

EXPRESSED RNA DATA 102 comprises published expressed sequence tags (EST) data, published mRNA data, as well as other published RNA data. SEQUENCED DNA DATA 104 comprises alphanumeric data representing genomic sequences and preferably including annotations such as information indicating the location of known protein coding regions relative to the genomic sequences.

PROTEIN FUNCTION DATA 106 comprises information from scientific publications e.g. physiological functions of known proteins and their connection, involvement and possible utility in treatment and diagnosis of various diseases.

EXPRESSED RNA DATA 102 and SEQUENCED DNA DATA 104 may preferably be obtained from data published by the National Center for Biotechnology Information (NCBI) at the National Institute of Health (NIH) (Jenuth, J. P. (2000). Methods Mol. Biol. 132:301-312 (2000), herein incorporated by reference) as well as from various other published data sources. PROTEIN FUNCTION DATA 106 may preferably be obtained from any one of numerous relevant published data sources, such as the Online Mendelian Inherited Disease In Man (OMIM™, Hamosh et al., Nucleic Acids Res. 30: 52-55 (2002)) database developed by John Hopkins University, and also published by NCBI (2000).

Prior to or during actual detection of BIOINFORMATICALLY DETECTED GROUP OF NOVEL OLIGONUCLEOTIDES 108 by the BIOINFORMATIC OLIGONUCLEOTIDE DETECTION ENGINE 100, BIOINFORMATIC OLIGONUCLEOTIDE DETECTION ENGINE TRAINING & VALIDATION FUNCTIONALITY 110 is operative. This functionality uses one or more known miRNA oligonucleotides as a training set to train the BIOINFORMATIC OLIGONUCLEOTIDE DETECTION ENGINE 100 to bioinformatically recognize miRNA-like oligonucleotides, and their respective potential target binding sites. BIOINFORMATIC OLIGONUCLEOTIDE DETECTION ENGINE TRAINING & VALIDATION FUNCTIONALITY 110 is further described hereinbelow with reference to FIG. 3.

The BIOINFORMATIC OLIGONUCLEOTIDE DETECTION ENGINE 100 preferably comprises several modules which are preferably activated sequentially, and are described as follows:

A NON-CODING GENOMIC SEQUENCE DETECTOR 112 operative to bioinformatically detect non-protein coding genomic sequences. The NON-CODING GENOMIC SEQUENCE DETECTOR 112 is further described herein below with reference to FIGS. 4A and 4B.

A HAIRPIN DETECTOR 114 operative to bioinformatically detect genomic 'hairpin-shaped' sequences, similar to GAM FOLDED PRECURSOR RNA (FIG. 1). The HAIRPIN DETECTOR 114 is further described herein below with reference to FIGS. 5A and 5B.

A DICER-CUT LOCATION DETECTOR 116 operative to bioinformatically detect the location on a GAM FOLDED PRECURSOR RNA which is enzymatically cut by DICER COMPLEX (FIG. 1), yielding diced GAM RNA. The DICER-CUT LOCATION DETECTOR 116 is further described herein below with reference to FIGS. 6A-6C.

A TARGET GENE BINDING-SITE DETECTOR 118 operative to bioinformatically detect target genes having binding sites, the nucleotide sequence of which is partially complementary to that of a given genomic sequence, such as a nucleotide sequence cut by DICER COMPLEX. The TARGET GENE BINDING-SITE DETECTOR 118 is further described hereinbelow with reference to FIGS. 7A and 7B.

A FUNCTION & UTILITY ANALYZER 120 operative to analyze the function and utility of target genes in order to identify target genes which have a significant clinical function and utility. The FUNCTION & UTILITY ANALYZER 120 is further described hereinbelow with reference to FIG. 8.

According to a preferred embodiment of the present invention the engine 100 may employ a cluster of 40 PCs (XEON®, 2.8 GHz, with 80 GB storage each), connected by Ethernet to 8 servers (2-CPU, XEON™ 1.2-2.2 GHz, with ~200 GB storage each), combined with an 8-processor server (8-CPU, Xeon 550 Mhz w/8 GB RAM) connected via 2 HBA fiber-channels to an EMC CLARIION™ 100-disks, 3.6 Terabyte storage device. A preferred embodiment of the present invention may also preferably comprise software which utilizes a commercial database software program, such as MICROSOFT™ SQL Server 2000. It is appreciated that the above mentioned hardware configuration is not meant to be limiting, and is given as an illustration only. The present invention may be implemented in a wide variety of hardware and software configurations.

The present invention discloses 6444 novel oligonucleotides of the GAM group of oligonucleotides, which have been detected bioinformatically and 726 novel polynucleotides of the GR group of polynucleotides, which have been detected bioinformatically. Laboratory confirmation of bioinformatically predicted oligonucleotides of the GAM group of oligonucleotides, and several bioinformatically predicted polynucleotides of the GR group of polynucleotides, is described hereinbelow with reference to FIGS. 12-15D.

Figure 3:
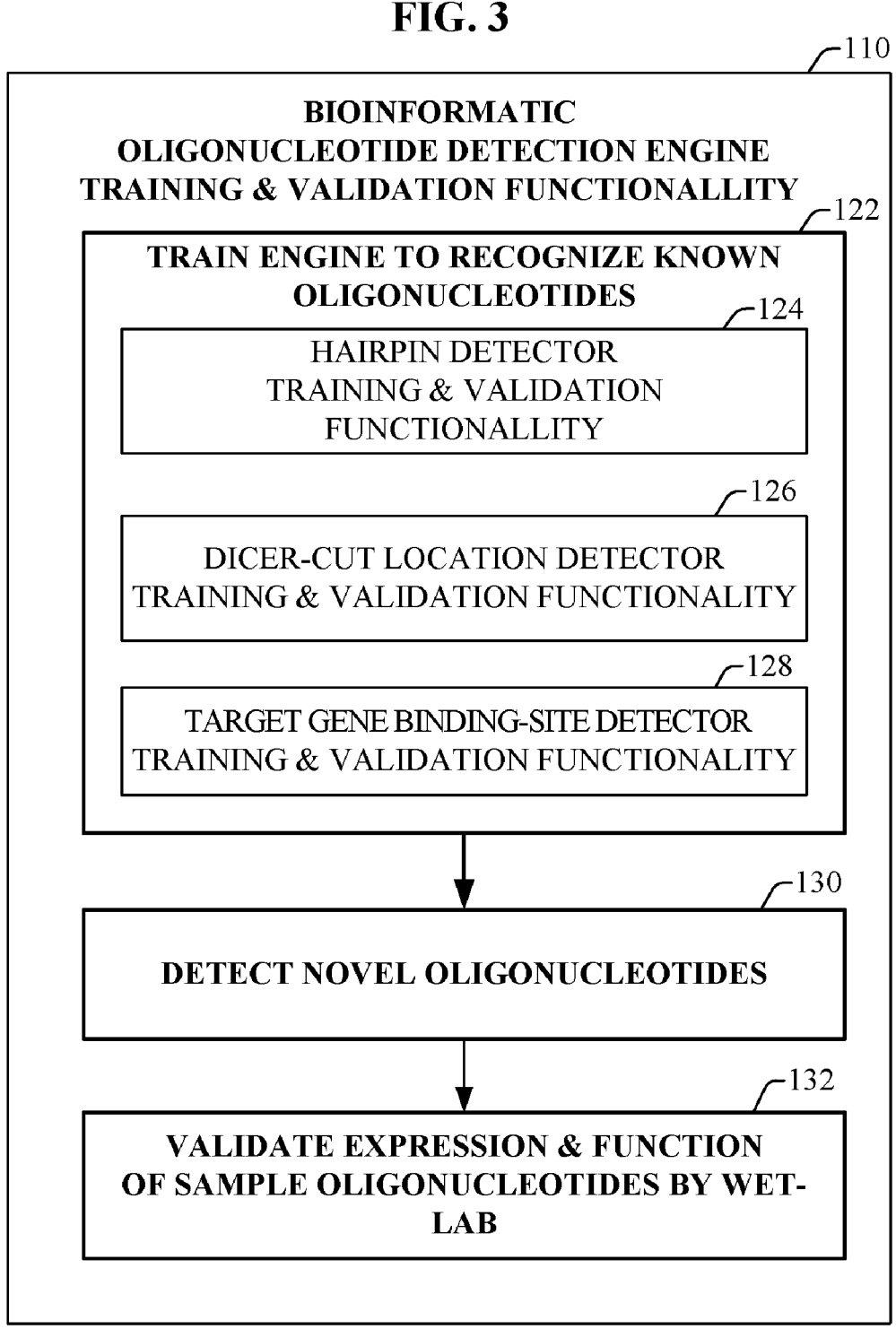
FIG. 3 is a simplified flowchart illustrating operation of a mechanism for training of a computer system to recognize the novel oligonucleotides of the present invention, which mechanism is constructed and operative in accordance with a preferred embodiment of the present invention.

Reference is now made to FIG. 3 which is a simplified flowchart illustrating operation of a preferred embodiment of the BIOINFORMATIC OLIGONUCLEOTIDE DETECTION ENGINE TRAINING & VALIDATION FUNCTIONALITY 110 described hereinabove with reference to FIG. 2.

BIOINFORMATIC OLIGONUCLEOTIDE DETECTION ENGINE TRAINING & VALIDATION FUNCTIONALITY 110 begins by training the BIOINFORMATIC OLIGONUCLEOTIDE DETECTION ENGINE 100 (FIG. 2) to recognize one or more known miRNA oligonucleotides, as designated by reference numeral 122. This training step comprises HAIRPIN DETECTOR TRAINING & VALIDATION FUNCTIONALITY 124, further described hereinbelow with reference to FIG. 5A, DICER-CUT LOCATION DETECTOR TRAINING & VALIDATION FUNCTIONALITY 126, further described hereinbelow with reference to FIGS. 6A and 6B, and TARGET GENE BINDING-SITE DETECTOR TRAINING & VALIDATION FUNCTIONALITY 128, further described hereinbelow with reference to FIG. 7A.

Next, the BIOINFORMATIC OLIGONUCLEOTIDE DETECTION ENGINE TRAINING & VALIDATION FUNCTIONALITY 110 is operative bioinformatically detect novel oligonucleotides, using BIOINFORMATIC OLIGONUCLEOTIDE DETECTION ENGINE 100 (FIG. 2), as designated by reference numeral 130. Wet lab experiments are preferably conducted in order to validate expression and preferably function of some samples of the novel oligonucleotides detected by the BIOINFORMATIC OLIGONUCLEOTIDE DETECTION ENGINE 100, as designated by reference numeral 132. FIGS. 13A-15D illustrate examples of wet-lab validation of sample novel human oligonucleotides bioinformatically detected in accordance with a preferred embodiment of the present invention.

Figure 4A:
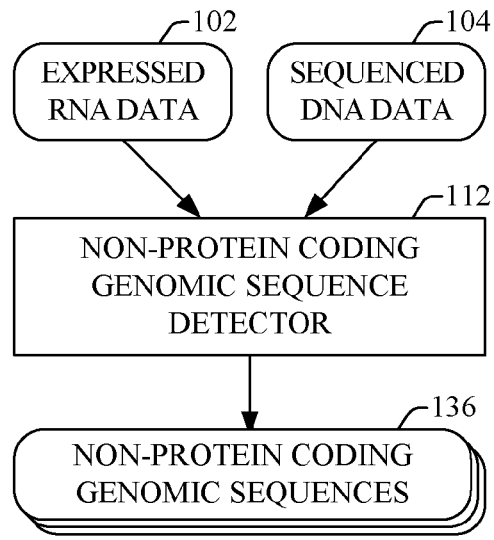
FIG. 4A is a simplified block diagram of a non-coding genomic sequence detector constructed and operative in accordance with a preferred embodiment of the present invention.

Reference is now made to FIG. 4A which is a simplified block diagram of a preferred implementation of the NON-CODING GENOMIC SEQUENCE DETECTOR 112 described hereinabove with reference to FIG. 2. The NON-PROTEIN CODING GENOMIC SEQUENCE DETECTOR 112 preferably receives at least two types of published genomic data: EXPRESSED RNA DATA 102 and SEQUENCED DNA DATA 104. The EXPRESSED RNA DATA 102 may include, inter alia, EST data, EST clusters data, EST genome alignment data and mRNA data. Sources for EXPRESSED RNA DATA 102 include NCBI dbEST, NCBI UniGene clusters and mapping data, and TIGR gene indices (Kirkness F. and Kerlavage, A. R., Methods Mol. Biol. 69:261-268 (1997)). SEQUENCED DNA DATA 104 may include sequence data (FASTA format files), and feature annotations (GenBank file format) mainly from NCBI databases. Based on the above mentioned input data, the NON-PROTEIN CODING GENOMIC SEQUENCE DETECTOR 112 produces a plurality of NON-PROTEIN CODING GENOMIC SEQUENCES 136. Preferred operation of the NON-PROTEIN CODING GENOMIC SEQUENCE DETECTOR 112 is described hereinbelow with reference to FIG. 4B.

Figure 4B:
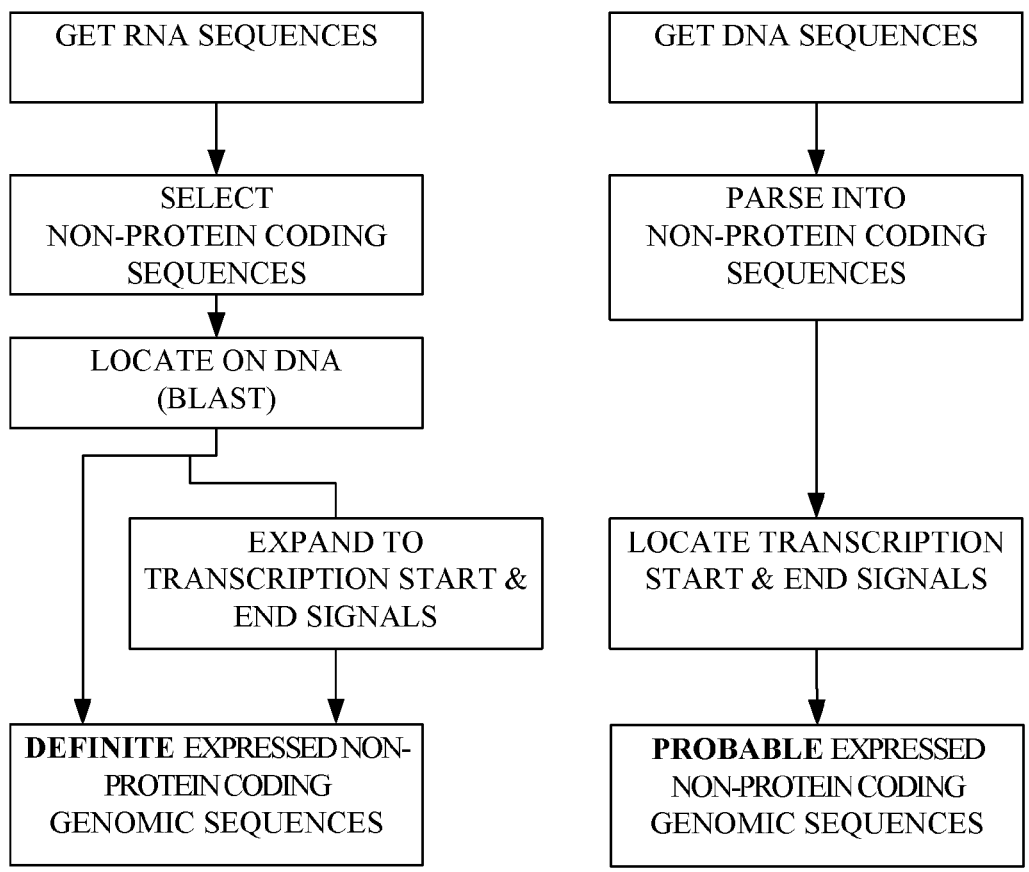
FIG. 4B is a simplified flowchart illustrating operation of a non-coding genomic sequence detector constructed and operative in accordance with a preferred embodiment of the present invention.

Reference is now made to FIG. 4B which is a simplified flowchart illustrating a preferred operation of the NON-CODING GENOMIC SEQUENCE DETECTOR 112 of FIG. 2. Detection of NON-PROTEIN CODING GENOMIC SEQUENCES 136, generally preferably progresses along one of the following two paths:

A first path for detecting NON-PROTEIN CODING GENOMIC SEQUENCES 136 (FIG. 4A) begins with receipt of a plurality of known RNA sequences, such as EST data. Each RNA sequence is first compared with known protein-coding DNA sequences, in order to select only those RNA sequences which are non-protein coding, i.e. intergenic or intronic sequences. This can preferably be performed by using one of many alignment algorithms known in the art, such as BLAST (Altschul et al., J. Mol. Biol. 215:403-410 (1990)). This sequence comparison preferably also provides localization of the RNA sequence on the DNA sequences.

Alternatively, selection of non-protein coding RNA sequences and their localization on the DNA sequences can be performed by using publicly available EST cluster data and genomic mapping databases, such as the UNIGENE database published by NCBI or the TIGR database. Such databases, map expressed RNA sequences to DNA sequences encoding them, find the correct orientation of EST sequences, and indicate mapping of ESTs to protein coding DNA regions, as is well known in the art. Public databases, such as TIGR, may also be used to map an EST to a cluster of ESTs, known in the art as Tentative Human Consensus and assumed to be expressed as one segment. Publicly available genome annotation databases, such as NCBIs GenBank, may also be used to deduce expressed intronic sequences.

Optionally, an attempt may be made to "expand" the non-protein RNA sequences thus found, by searching for transcription start and end signals, respectively upstream and downstream of the location of the RNA on the DNA, as is well known in the art.

A second path for detecting NON-PROTEIN CODING GENOMIC SEQUENCES 136 (FIG. 4A) begins with receipt of DNA sequences. The DNA sequences are parsed into non protein coding sequences, using published DNA annotation data, by extracting those DNA sequences which are between known protein coding sequences. Next, transcription start and end signals are sought. If such signals are found, and depending on their robustness, probable expressed non-protein coding genomic sequences are obtained. Such approach is especially useful for identifying novel GAM oligonucleotides which are found in proximity to other known miRNA oligonucleotides, or other wet-lab validated GAM oligonucleotides. Since, as described hereinbelow with reference to FIG. 9, GAM oligonucleotides are frequently found in clusters; sequences located near known miRNA oligonucleotides are more likely to contain novel GAM oligonucleotides. Optionally, sequence orthology, i.e. sequence conservation in an evolutionary related species, may be used to select genomic sequences having a relatively high probability of containing expressed novel GAM oligonucleotides. It is appreciated that in detecting non-human GAM oligonucleotides of the present invention the BIOINFORMATIC OLIGONUCLEOTIDE DETECTION ENGINE 100 utilizes the input genomic sequences, without filtering protein coding regions detected by the NON-CODING GENOMIC SEQUENCE DETECTOR 112, hence NON-PROTEIN CODING GENOMIC SEQUENCES 136 refers to GENOMIC SEQUENCES only.

Figure 5A:
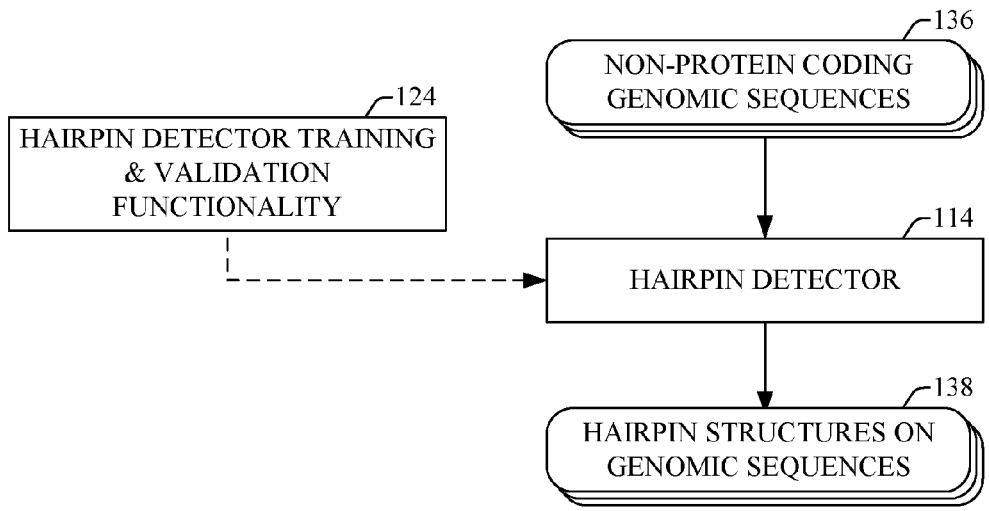
FIG. 5A is a simplified block diagram of a hairpin detector constructed and operative in accordance with a preferred embodiment of the present invention.

Reference is now made to FIG. 5A which is a simplified block diagram of a preferred implementation of the HAIRPIN DETECTOR 114 described hereinabove with reference to FIG. 2.

The goal of the HAIRPIN DETECTOR 114 is to detect hairpin-shaped genomic sequences, similar to those of known miRNA oligonucleotides. A hairpin-shaped genomic sequence is a genomic sequence, having a first half which is at least partially complementary to a second half thereof, which causes the halves to folds onto themselves, thereby forming a hairpin structure, as mentioned hereinabove with reference to FIG. 1.

The HAIRPIN DETECTOR 114 (FIG. 2) receives a plurality of NON-PROTEIN CODING GENOMIC SEQUENCES 136 (FIG. 4A). Following operation of HAIRPIN DETECTOR TRAINING & VALIDATION FUNCTIONALITY 124 (FIG. 3), the HAIRPIN DETECTOR 114 is operative to detect and output hairpin-shaped sequences, which are found in the NON-PROTEIN CODING GENOMIC SEQUENCES 136. The hairpin-shaped sequences detected by the HAIRPIN DETECTOR 114 are designated HAIRPINS STRUCTURES ON GENOMIC SEQUENCES 138. A preferred mode of operation of the HAIRPIN DETECTOR 114 is described hereinbelow with reference to FIG. 5B.

HAIRPIN DETECTOR TRAINING & VALIDATION FUNCTIONALITY 124 includes an iterative process of applying the HAIRPIN DETECTOR 114 to known hairpin shaped miRNA precursor sequences, calibrating the HAIRPIN DETECTOR 114 such that it identifies a training set of known hairpin-shaped miRNA precursor sequences, as well as other similarly hairpin-shaped sequences. In a preferred embodiment of the present invention, the HAIRPIN DETECTOR TRAINING & VALIDATION FUNCTIONALITY 124 trains the HAIRPIN DETECTOR 114 and validates each of the steps of operation thereof described hereinbelow with reference to FIG. 5B The HAIRPIN DETECTOR TRAINING & VALIDATION FUNCTIONALITY 124 preferably uses two sets of data: the aforesaid training set of known hairpin-shaped miRNA precursor sequences, such as hairpin-shaped miRNA precursor sequences of 440 miRNA oligonucleotides of *H. sapiens, M. musculus, C. elegans, C. Brigssae* and *D. Melanogaster*, annotated in the RFAM database (Griffiths-Jones 2003), and a background set of about 1000 hairpin-shaped sequences found in expressed non-protein coding human genomic sequences. The background set is expected to comprise some valid, previously undetected hairpin-shaped miRNA-like precursor sequences, and many hairpin-shaped sequences which are not hairpin-shaped miRNA-like precursors.

In a preferred embodiment of the present invention the efficacy of the HAIRPIN DETECTOR 114 (FIG. 2) is confirmed. For example, when a similarity threshold is chosen such that 87% of the known hairpin-shaped miRNA precursors are successfully predicted, only 21.8% of the 1000 background set of hairpin-shaped sequences are predicted to be hairpin-shaped miRNA-like precursors.

Figure 5B:
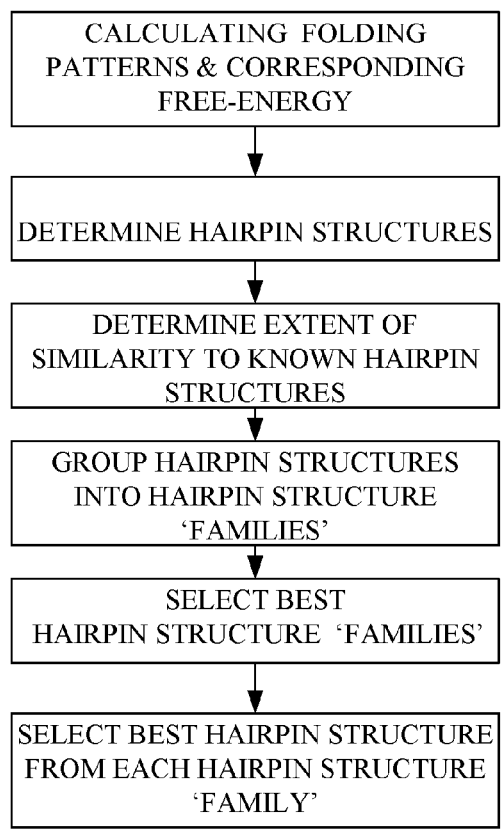
FIG. 5B is a simplified flowchart illustrating operation of a hairpin detector constructed and operative in accordance with a preferred embodiment of the present invention.

Reference is now made to FIG. 5B which is a simplified flowchart illustrating preferred operation of the HAIRPIN DETECTOR 114 of FIG. 2. The HAIRPIN DETECTOR 114 preferably initially uses a secondary structure folding algorithm based on free-energy minimization, such as the MFOLD algorithm, described in Mathews et al. J. Mol. Biol. 288:911-940 (1999) and Zuker, M. Nucleic Acids Res. 31: 3406-3415 (2003), the disclosure of which is hereby incorporated by reference. This algorithm is operative to calculate probable secondary structure folding patterns of the NON-PROTEIN CODING GENOMIC SEQUENCES 136 (FIG. 4A) as well as the free-energy of each of these probable secondary folding patterns. The secondary structure folding algorithm, such as the MFOLD algorithm (Mathews, 1997; Zuker 2003), typically provides a listing of the base-pairing of the folded shape, i.e. a listing of each pair of connected nucleotides in the sequence.

Next, the HAIRPIN DETECTOR 114 analyzes the results of the secondary structure folding patterns, in order to determine the presence and location of hairpin folding structures. The goal of this second step is to assess the base-pairing listing provided by the secondary structure folding algorithm, in order to determine whether the base-pairing listing describes one or more hairpin type bonding pattern. Preferably, sequence segment corresponding to a hairpin structure is then separately analyzed by the secondary structure folding algorithm in order to determine its exact folding pattern and free-energy.

The HAIRPIN DETECTOR 114 then assesses the hairpin structures found by the previous step, comparing them to hairpin structures of known miRNA precursors, using various characteristic hairpin structure features such as its free-energy and its thermodynamic stability, the amount and type of mismatched nucleotides and the existence of sequence repeat-elements, number of mismatched nucleotides in positions 18-22 counting from loop, and Percent of G nucleotide. Only hairpins that bear statistically significant resemblance to the training set of hairpin structures of known miRNA precursors, according to the abovementioned parameters, are accepted.

In a preferred embodiment of the present invention, similarity to the training set of hairpin structures of known miRNA precursors is determined using a "similarity score" which is calculated using a multiplicity of terms, where each term is a function of one of the abovementioned hairpin structure features. The parameters of each function are found heuristically from the set of hairpin structures of known miRNA precursors, as described hereinabove with reference to HAIRPIN DETECTOR TRAINING & VALIDATION FUNCTIONALITY 124 (FIG. 3). The selection of the features and their function parameters is optimized so as to achieve maximized separation between the distribution of similarity scores validated miRNA-precursor hairpin structures, and the distribution of similarity scores of hairpin structures detected in the background set mentioned hereinabove with reference to FIG. 5B.

In an alternative preferred embodiment of the present invention, the step described in the preceding paragraph may be split into two stages. A first stage implements a simplified scoring method, typically based on thresholding a subset of the hairpin structure features described hereinabove, and may employ a minimum threshold for hairpin structure length and a maximum threshold for free energy. A second stage is preferably more stringent, and preferably employs a full calculation of the weighted sum of terms described hereinabove. The second stage preferably is performed only on the subset of hairpin structures that survived the first stage.

The HAIRPIN DETECTOR 114 also attempts to select hairpin structures whose thermodynamic stability is similar to that of hairpin structures of known miRNA precursors. This may be achieved in various ways. A preferred embodiment of the present invention utilizes the following methodology, preferably comprising three logical steps:

First, the HAIRPIN DETECTOR 114 attempts to group hairpin structures into "families" of closely related hairpin structures. As is known in the art, a secondary structure folding algorithm typically provides multiple alternative folding patterns, for a given genomic sequence and indicates the free energy of each alternative folding pattern. It is a particular feature of the present invention that the HAIRPIN DETECTOR 114 preferably assesses the various hairpin structures appearing in the various alternative folding patterns and groups' hairpin structures which appear at identical or similar sequence locations in various alternative folding patterns into common sequence location based "families" of hairpins. For example, all hairpin structures whose center is within 7 nucleotides of each other may be grouped into a family". Hairpin structures may also be grouped into a family" if their nucleotide sequences are identical or overlap to a predetermined degree.

It is also a particular feature of the present invention that the hairpin structure "families" are assessed in order to select only those families which represent hairpin structures that are as thermodynamically stable as those of hairpin structures of known miRNA precursors. Preferably only families which are represented in at least a selected majority of the alternative secondary structure folding patterns, typically 65%, 80% or 100% are considered to be sufficiently stable. Our tests suggest that only about 50% of the hairpin structures, predicted by the MFOLD algorithm with default parameters, are members of sufficiently stable families, comparing to about 90% of the hairpin structures that contain known miRNAs. This percent depends on the size of the fraction that was fold. In an alternative embodiment of the present invention we use fractions of size 1000 nts as preferable size. Different embodiment uses other sizes of genomics sequences, more or less strict demand for representation in the alternative secondary structure folding patterns.

It is an additional particular feature of the present invention that the most suitable hairpin structure is selected from each selected family. For example, a hairpin structure which has the greatest similarity to the hairpin structures appearing in alternative folding patterns of the family may be preferred. Alternatively or additionally, the hairpin structures having relatively low free energy may be preferred.

Alternatively or additionally considerations of homology to hairpin structures of other organisms and the existence of clusters of thermodynamically stable hairpin structures located adjacent to each other along a sequence may be important in selection of hairpin structures. The tightness of the clusters in terms of their location and the occurrence of both homology and clusters may be of significance.

Figure 6A:
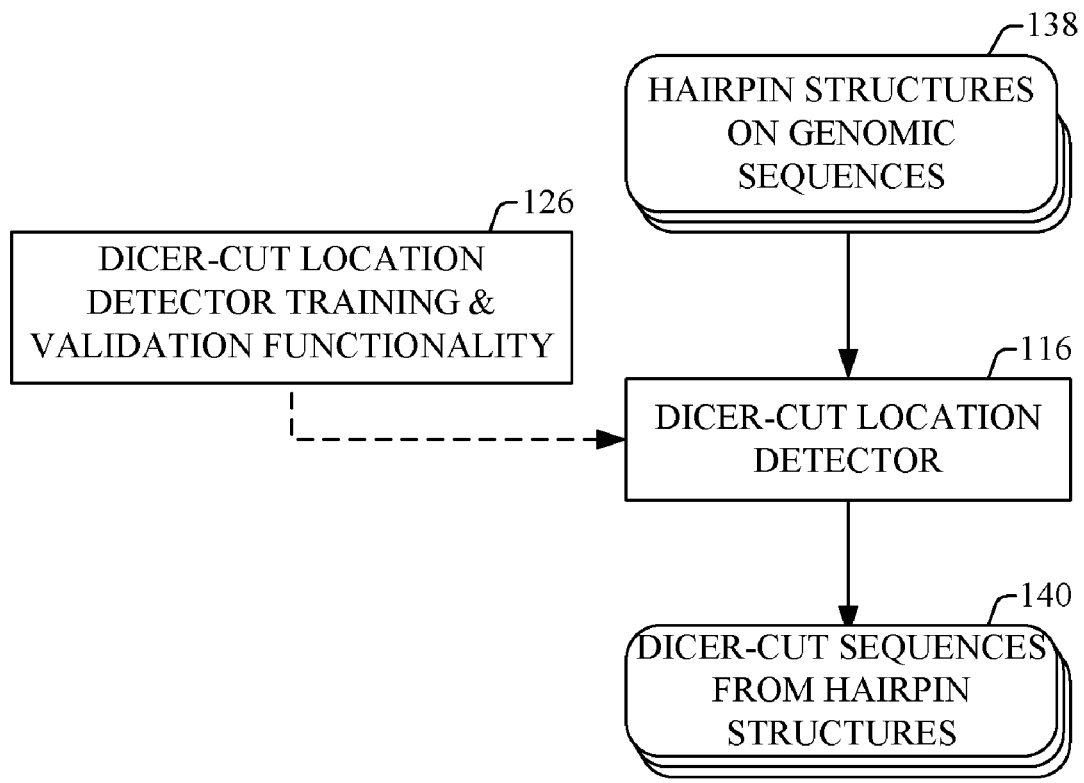
FIG. 6A is a simplified block diagram of a dicer-cut location detector constructed and operative in accordance with a preferred embodiment of the present invention.
Figure 6B:
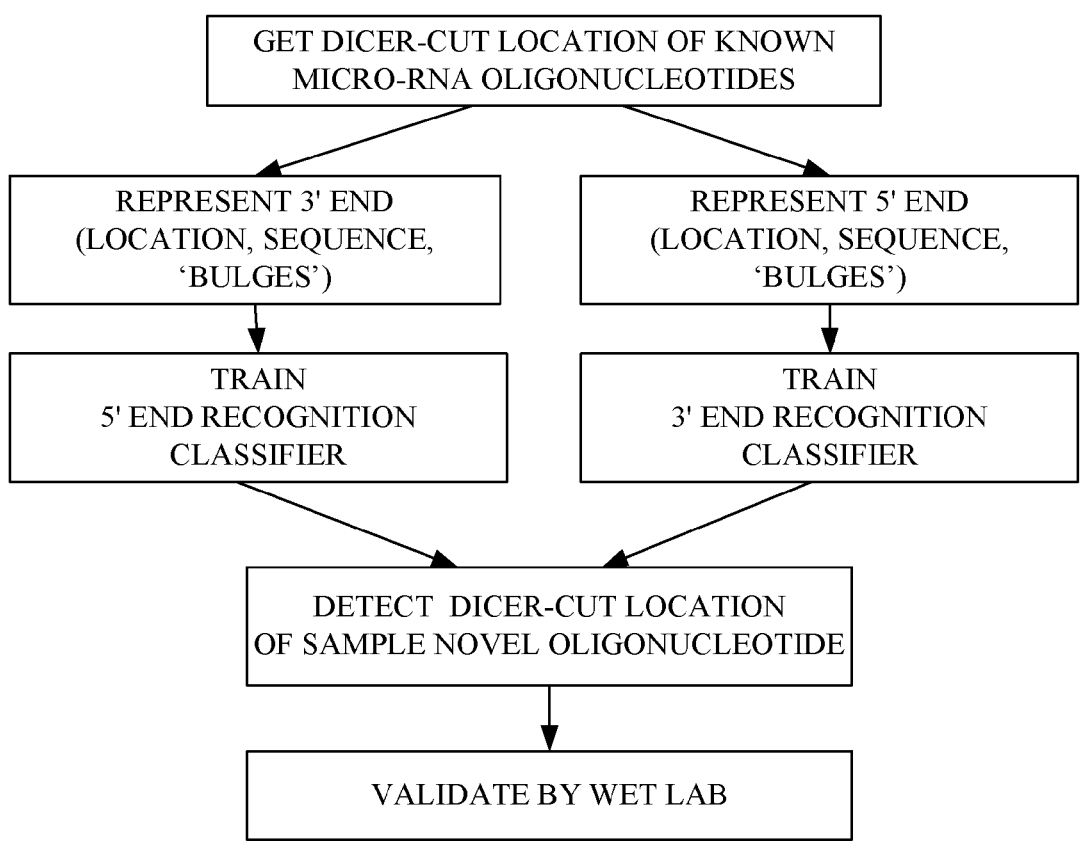
FIG. 6B is a simplified flowchart illustrating training of a dicer-cut location detector constructed and operative in accordance with a preferred embodiment of the present invention.
Figure 6C:
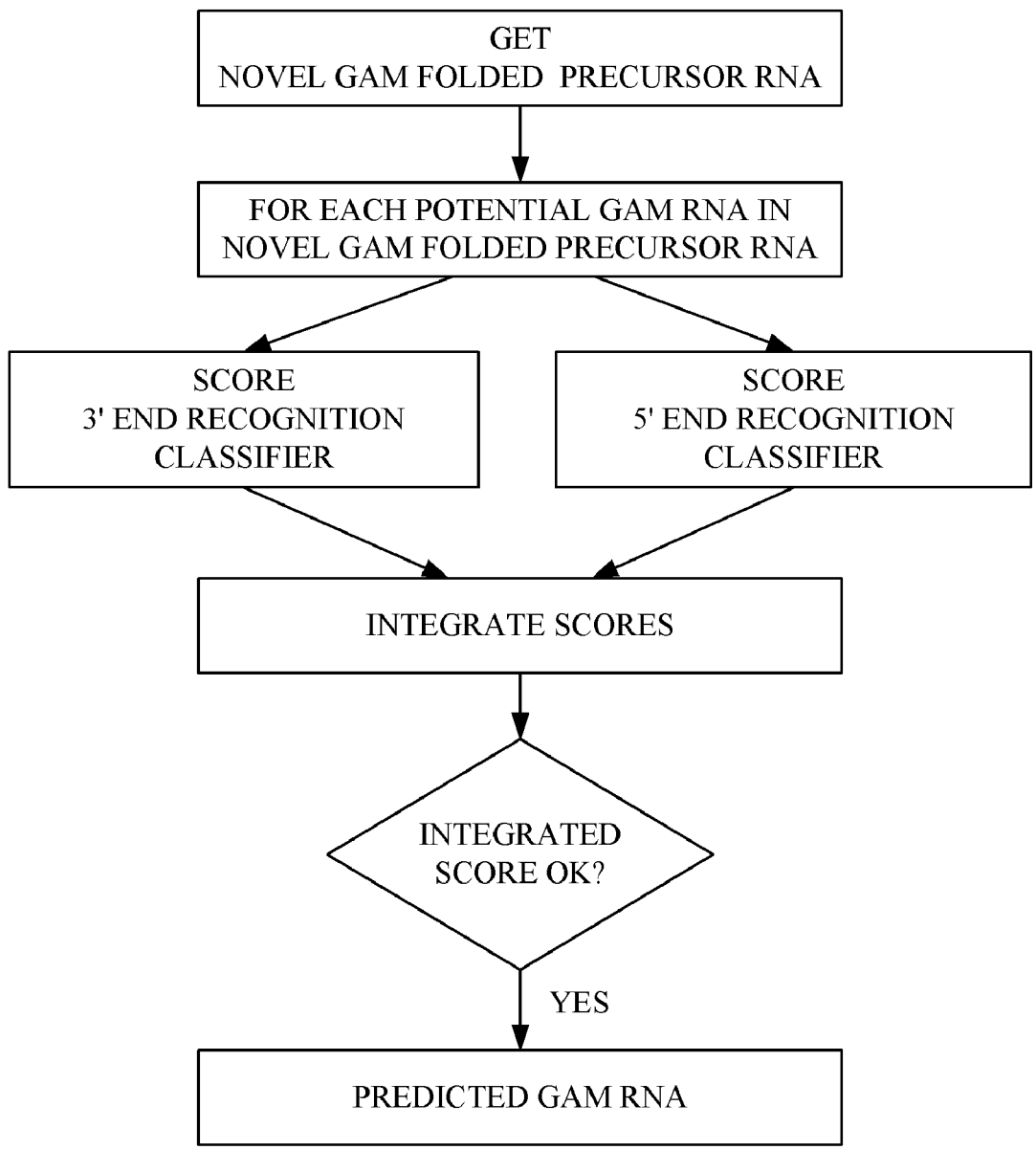
FIG. 6C is a simplified flowchart illustrating operation of a dicer-cut location detector constructed and operative in accordance with a preferred embodiment of the present invention.

Reference is now made to FIGS. 6A-6C which together describe the structure and operation of the DICER-CUT LOCATION DETECTOR 116, described hereinabove with FIG. 2.

FIG. 6A is a simplified block diagram of a preferred implementation of the DICER-CUT LOCATION DETECTOR 116. The goal of the DICER-CUT LOCATION DETECTOR 116 is to detect the location in which the DICER COMPLEX, described hereinabove with reference to FIG. 1, dices GAM FOLDED PRECURSOR RNA, yielding GAM RNA.

The DICER-CUT LOCATION DETECTOR 116 therefore receives a plurality of HAIRPIN STRUCTURES ON GENOMIC SEQUENCES 138 (FIG. 5A), and following operation of DICER-CUT LOCATION DETECTOR TRAINING & VALIDATION FUNCTIONALITY 126 (FIG. 3), is operative to detect a plurality of DICER-CUT SEQUENCES FROM HAIRPIN STRUCTURES 140.

Reference is now made to FIG. 6B which is a simplified flowchart illustrating a preferred implementation of DICER-CUT LOCATION DETECTOR TRAINING & VALIDATION FUNCTIONALITY 126.

A general goal of the DICER-CUT LOCATION DETECTOR TRAINING & VALIDATION FUNCTIONALITY 126 is to analyze the dicer-cut locations of known diced miRNA on respective hairpin shaped miRNA precursors in order to determine a common pattern in these locations, which can be used to predict dicer cut locations on GAM folded precursor RNAs.

The dicer-cut locations of known miRNA precursors are obtained and studied. Locations of the 5' and/or 3' ends of the known diced miRNAs are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor.

One or more of the foregoing location metrics may be employed in the training and validation functionality. Additionally, metrics related to the nucleotide content of the diced miRNA and/or of the hairpin shaped miRNA precursor may be employed.

In a preferred embodiment of the present invention, DICER-CUT LOCATION DETECTOR TRAINING & VALIDATION FUNCTIONALITY 126 preferably employs standard machine learning techniques known in the art of machine learning for analysis of existing patterns in a given "training set" of examples. These techniques are capable, to a certain degree, of detecting similar patterns in other, previously unseen examples. Such machine learning techniques include, but are not limited to neural networks, Bayesian networks, Support Vector Machines (SVM), Genetic Algorithms, Markovian modeling, Maximum Likelihood modeling, Nearest Neighbor algorithms, Decision trees and other techniques, as is well known in the art.

In accordance with one embodiment of the present invention, machine learning predictors, such as a Support Vector Machine (SVM) predictor, are applied to the aforementioned training set and are operative, for example to test every possible nucleotide on a hairpin as a candidate for being the 5' end or the 3' end of a diced GAM RNA. More preferred machine learning predictors include predictors based on Nearest Neighbor, Bayesian modeling, and K-nearest-neighbor algorithms. A training set of the known miRNA precursor sequences is preferably used for training multiple separate classifiers or predictors, each of which produces a model for the 5' and/or 3' end locations of a diced miRNA with respect to its hairpin precursor. The models take into account one or more of the various miRNA location metrics described above.

Performance of the resulting predictors, evaluated on the abovementioned validation set of 440 published miRNAs using k-fold cross validation (Mitchell, 1997) with k=3, is found to be as follows: in 70% of known miRNAs 5'-end location is correctly determined by an SVM predictor within up to 2 nucleotides; a Nearest Neighbor (EDIT DISTANCE) predictor achieves 56% accuracy (247/440); a Two-Phased predictor that uses Bayesian modeling (TWO PHASED) achieves 80% accuracy (352/440), when only the first phase is used. When the second phase (strand choice) is implemented by a nave Bayesian model the accuracy is 55% (244/440), and when the K-nearest-neighbor modeling is used for the second phase, 374/440 decision are made and the accuracy is 65% (242/374). A K-nearest-neighbor predictor (FIRST-K) achieves 61% accuracy (268/440). The accuracies of all predictors are considerably higher on top scoring subsets of published miRNA.

Finally, in order to validate the efficacy and accuracy of the DICER-CUT LOCATION DETECTOR 116, a sample of novel oligonucleotides detected thereby is preferably selected, and validated by wet lab. Laboratory results validating the efficacy of the DICER-CUT LOCATION DETECTOR 116 are described hereinbelow with reference to FIGS. 12-15D.

Reference is now made to FIG. 6C which is a simplified flowchart illustrating operation of DICER-CUT LOCATION DETECTOR 116 (FIG. 2), constructed and operative in accordance with a preferred embodiment of the present invention. The DICER CUT LOCATION DETECTOR 116 preferably comprises a machine learning computer program module, which is trained to recognize dicer-cut locations on known hairpin-shaped miRNA precursors, and based on this training, is operable to detect dicer-cut locations of novel GAM RNAs (FIG. 1) on GAM FOLDED PRECURSOR RNAs (FIG. 1). In a preferred embodiment of the present invention, the dicer-cut location module preferably utilizes machine learning algorithms, such as known Support Vector Machine (SVM) and more preferably: known Bayesian modeling, Nearest Neighbors, and K-nearest-neighbor algorithms.

When initially assessing a novel GAM FOLDED PRECURSOR RNA, all 19-24 nucleotide long segments thereof are initially considered as "potential GAM RNAs", since the dicer-cut location is initially unknown.

For each such potential GAM RNA, the location of its 5' end or the locations of its 5' and 3' ends are scored by at least one recognition classifier or predictor.

In a preferred embodiment of the present invention, the DICER-CUT LOCATION DETECTOR 116 (FIG. 2) may use a Support Vector Machine predictor trained on and operating on features such as the following:

Locations of the 5' and/or 3' ends of the known diced miRNAs, which are preferably represented by their respective distances from the 5 end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In another preferred embodiment of the present invention, the DICER-CUT LOCATION DETECTOR 116 (FIG. 2) preferably employs an "EDIT DISTANCE" predictor, which seeks sequences that are similar to those of known miRNAs, utilizing a Nearest Neighbor algorithm, where a similarity metric between two sequences is a variant of the Edit Distance algorithm (Gusfield, 1997). The EDIT DISTANCE predictor is based on an observation that miRNA oligonucleotides tend to form clusters, the members of which show marked sequence similarity.

In yet another preferred embodiment of the present invention, the DICER-CUT LOCATION DETECTOR 116 (FIG. 2) preferably uses a "TWO PHASE" predictor, which predicts the dicer-cut location in two distinct phases: (a) selecting a double-stranded segment of the GAM FOLDED PRECURSOR RNA (FIG. 1) comprising the GAM RNA by nave Bayesian modeling and (b) detecting which strand of the double-stranded segment contains GAM RNA (FIG. 1) by employing either nave or by K-nearest-neighbor modeling. K-nearest-neighbor modeling is a variant of the 'FIRST-K' predictor described hereinbelow, with parameters optimized for this specific task. The 'TWO PHASE' predictor may be operated in two modes: either utilizing only the first phase and thereby producing two alternative dicer-cut location predictions, or utilizing both phases and thereby producing only one final dicer-cut location.

In still another preferred embodiment of the present invention, the DICER-CUT LOCATION DETECTOR 116 preferably uses a "FIRST-K" predictor, which utilizes a K-nearest-neighbor algorithm. The similarity metric between any two sequences is 1−E/L, where L is a parameter, preferably 8-10 and E is the edit distance between the two sequences, taking into account only the first L nucleotides of each sequence. If the K-nearest-neighbor scores of two or more locations on the GAM FOLDED PRECURSOR RNA (FIG. 1) are not significantly different, these locations are further ranked by a Bayesian model, similar to the one described hereinabove.

The TWO PHASE and FIRST-K predictors preferably are trained on and operate on features such as the following:

Locations of the 5' and/or 3' ends of the known diced miRNAs, which are preferably represented by their respective distances from the 5' end of the corresponding hairpin shaped miRNA precursor. Additionally or alternatively, the 5' and/or 3' ends of the known diced miRNAs are preferably represented by the relationship between their locations and the locations of one or more nucleotides along the hairpin shaped miRNA precursor. Additionally or alternatively, the 5' and/or 3' ends of the known diced miRNAs are preferably represented by the relationship between their locations and the locations of one or more bound nucleotide pairs along the hairpin shaped miRNA precursor. Additionally or alternatively, the 5' and/or 3' ends of the known diced miRNAs are preferably represented by the relationship between their locations and the locations of one or more mismatched nucleotide pairs along the hairpin shaped miRNA precursor. Additionally or alternatively, the 5' and/or 3' ends of the known diced miRNAs are preferably represented by the relationship between their locations and the locations of one or more unmatched nucleotides along the hairpin shaped miRNA precursor. Additionally or alternatively, locations of the 5' and/or 3' ends of the known diced miRNAs are preferably represented by their respective distances from the loop located at the center of the corresponding hairpin shaped miRNA precursor; and secondarily Metrics related to the nucleotide content of the diced miRNA and/or of the hairpin shaped miRNA precursor.

In accordance with an embodiment of the present invention scores of two or more of the abovementioned classifiers or predictors are integrated, yielding an integrated score for each "potential GAM RNA". As an example, FIG. 6C illustrates integration of scores from two classifiers, a 3' end recognition classifier and a 5' end recognition classifier, the scores of which are integrated to yield an integrated score. Most preferably, the INTEGRATED SCORE of FIG. 6C preferably implements a "best-of-breed" approach employing a pair of classifiers and accepting only "potential GAM RNAs" that score highly on one of the above mentioned "EDIT DISTANCE", or "TWO-PHASE" predictors. In this context, "high scores" means scores which have been demonstrated to have low false positive value when scoring known miRNA oligonucleotides. Alternatively, the INTEGRATED SCORE may be derived from operation of more or less than two classifiers.

The INTEGRATED SCORE is evaluated as follows: (a) the "potential GAM RNA" having the highest score is preferably taken to be the most probable GAM RNA, and (b) if the integrated score of this most probable GAM RNA is higher than a pre-defined threshold, then the most probable GAM RNA is accepted as a PREDICTED GAM RNA. Preferably, this evaluation technique is not limited to the highest scoring potential GAM RNA.

As a final optional stage we may filter PREDICTED GAM RNAs with low complexity, which have high probability to be part of repeated element in the DNA (for example ATATATA sequences). For each PREDICTED GAM RNA sequence we count the number of occurrences of each 2 nucleotides combination (AA, AT, AC), we filter out sequences where the sum of the most 2 probable combination is higher then 9. Using this criteria we filter 2% of the known miRNA and around 30% of the PREDICTED GAM RNAs.

Figure 7A:
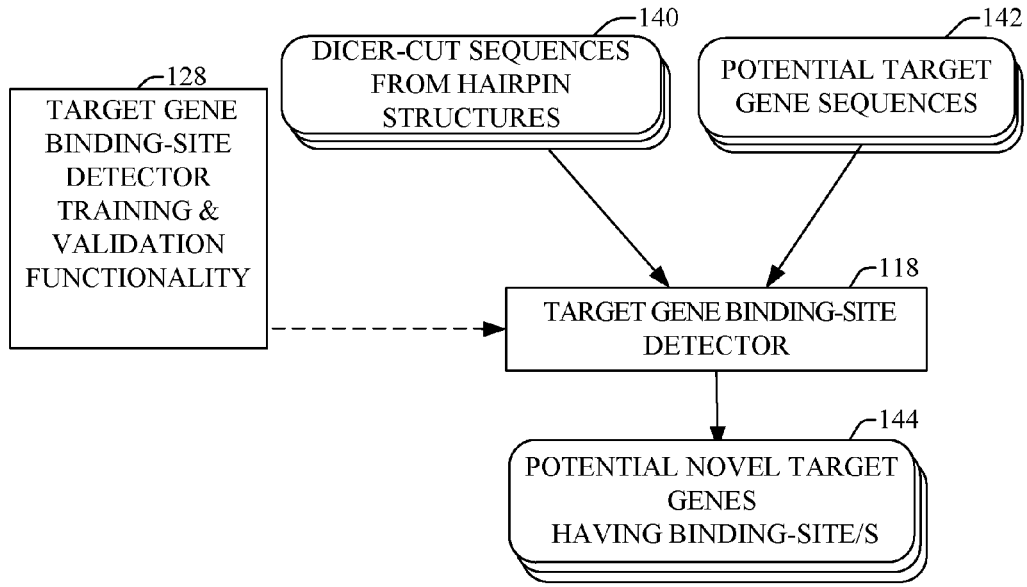
FIG. 7A is a simplified block diagram of a target gene binding-site detector constructed and operative in accordance with a preferred embodiment of the present invention.

Reference is now made to FIG. 7A which is a simplified block diagram of a preferred implementation of the TARGET GENE BINDING-SITE DETECTOR 118 described hereinabove with reference to FIG. 2. The goal of the TARGET GENE BINDING-SITE DETECTOR 118 is to detect one or more binding sites such as BINDING SITE I, BINDING SITE II and BINDING SITE III (FIG. 1) located in 3' untranslated regions of the mRNA of a known gene, the nucleotide sequence of which binding sites is partially or fully complementary to a GAM RNA, thereby determining that the above mentioned known gene is a target gene thereof.

The TARGET GENE BINDING-SITE DETECTOR 118 (FIG. 2) receives a plurality of DICER-CUT SEQUENCES FROM HAIRPIN STRUCTURES 140 (FIG. 6A), and a plurality of POTENTIAL TARGET GENE SEQUENCES 142 which are derived from SEQUENCED DNA DATA 104 (FIG. 2).

TARGET GENE BINDING-SITE DETECTOR TRAINING & VALIDATION FUNCTIONALITY 128 (FIG. 3) is operative to train the TARGET GENE BINDING-SITE DETECTOR 118 on known miRNAs and their respective target genes and to build a background model for evaluation of a P value for the TARGET GENE BINDING-SITE DETECTOR 118 results It Construct the model by analyzing both heuristically and computationally the results of the TARGET GENE BINDING-SITE DETECTOR 118.

Following operation of TARGET GENE BINDING-SITE DETECTOR TRAINING & VALIDATION FUNCTIONALITY 128 (FIG. 3), the TARGET GENE BINDING-SITE DETECTOR 118 is operative to detect a plurality of POTENTIAL NOVEL TARGET GENES HAVING BINDING-SITE/S 144 the nucleotide sequence of which is partially or fully complementary to that of each of the plurality of DICER-CUT SEQUENCES FROM HAIRPIN STRUCTURES 140. Preferred operation of the TARGET GENE BINDING-SITE DETECTOR 118 is further described hereinbelow with reference to FIG. 7B.

Figure 7B:
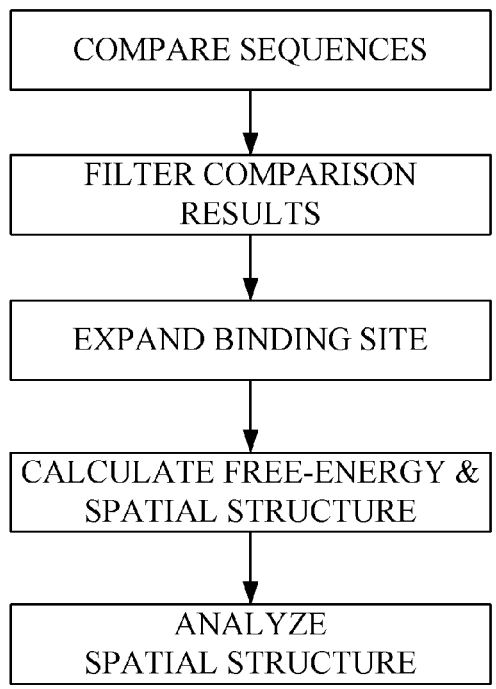
FIG. 7B is a simplified flowchart illustrating operation of a target gene binding-site detector constructed and operative in accordance with a preferred embodiment of the present invention.

Reference is now made to FIG. 7B which is a simplified flowchart illustrating a preferred operation of the TARGET GENE BINDING-SITE DETECTOR 118 of FIG. 2. In a preferred embodiment of the present invention, the TARGET GENE BINDING-SITE DETECTOR 118 employs a match search tool, described hereinbelow, in order to compare the nucleotide sequence of each of the plurality of DICER-CUT SEQUENCES FROM HAIRPIN STRUCTURES 140 (FIG. 6A), to the POTENTIAL TARGET GENE SEQUENCES 142 (FIG. 7A), such as 3 untranslated regions of known mRNAs, in order to find crude potential matches. Alternatively, a sequence comparison algorithm such as BLAST can be used.

The match search tool compare the DICER-CUT SEQUENCES FROM HAIRPIN STRUCTURES 140 (FIG. 7A) to POTENTIAL TARGET GENE SEQUENCES 142 (FIG. 7A). the methodology of the match search tool is to match Nucleotides 1:8 of DICER-CUT SEQUENCES FROM HAIRPIN STRUCTURES 140 (FIG. 7A) to POTENTIAL TARGET GENE SEQUENCES 142 (FIG. 7A). The results are preferably filtered to allow at most 1 edit distance between the DICER-CUT SEQUENCES FROM HAIRPIN STRUCTURES 140 (FIG. 7A) complementary sequence and POTENTIAL TARGET GENE SEQUENCES 142 (FIG. 7A).

In a preferred implementation of the match search tool, it first calculates two preprocess data structures: the first, store for every 9 nts sequences all its appearances in the POTENTIAL TARGET GENE SEQUENCES 142 (FIG. 7A).

The second is a map of all the 8 nts sequence to 9 nts sequences that can be accepted by adding one nucleotide and performing one or less editing actions to the 8 nts complementary sequence. This two data structures help to improve performance and to perform the binding site filtering stage as an integral part of the search. The match search tool in this implementation returns for every DICER-CUT SEQUENCES FROM HAIRPIN STRUCTURES 140 (FIG. 7A all the appearances of the 9 nts sequence in the POTENTIAL TARGET GENE SEQUENCES 142 (FIG. 7A) that are calculated using the second, describe hereinabove, data structure from its first 8 nts. The 9 nts sequences appearances are the potentially 3 of the POTENTIAL TARGET GENE SEQUENCES 142 (FIG. 7A) binding site of each DICER-CUT SEQUENCES FROM HAIRPIN STRUCTURES 140 (FIG. 7A Next the binding sites are expanded, and determinations are made whether if nucleotide sequences immediately upstream to the binding sites 3 part matches with the 3' end of the DICER-CUT SEQUENCES FROM HAIRPIN STRUCTURES. The alignment of the binding site 5 part is made by the alignment algorithm with specific weighting parameters describes hereinbelow with reference to FIG. 5). Alternatively the alignment can include also the 3 part of the binding site.

The alignment algorithm (implemented here) with specific weighting parameters. The weighting parameters are based on analyze of known miRNA binding sites (references: Wightman et al. Cell 1993, Moss Cell 1997, Reinhart Nature 2000, Abrahante Developmental Cell 2003 and Lin Developmental Cell 2003, Brennecke Cell 2003, Stark PLOS 2003, lewis et al. Cell 2003). It was heuristically found to best distinguish between known miRNA binding sites and sequences which are known not to be miRNA binding sites.

According to a preferred embodiment of the present invention a good matching at 5' end of the miRNA (nucleotides 1-8), and at 3' end of the miRNA, (the last 9 nucleotides) is required. The matching at 5' end is crucial for the binding while the 3' end binding is less important but can compensate on few mismatches at the 5'. The nucleotides at the middle of the miRNA have no punishment for any editing operation (reference: Doench et al. Gene and Development 2004). In this preferred embodiment the alignment of the 5 end of the miRNA (3 of the binding site) is a result of the match search tool, while the middle and 3 miRNA (5 of the binding site) is done by the alignment algorithm. The alignment is a combination of both. Alternatively, the alignment is done for all the miRNA and all the binding site sequence. The alignment algorithm finds the lowest free-energy spatial structure and heuristic constrain that were found to distinct the known binding sites in the best way. The alignment yields 2 scores for 5' end and 3' end. Each score represents the inverse of its probability to obtain such or higher score by running random sequences, with 22 nucleotides length and same base composition as known miRNA, with randomly chosen 3 un translated region sequences. The final score is the multiplicity of the two scores.

The binding site detector, then analyze the spatial structure of the miRNA with all its potential target gene 3 un translated region. It assesses the list of binding sites of each miRNA—Target gene pair with their positions and respective scores. The TARGET GENE BINDING-SITE DETECTOR 118 (FIG. 7A) then uses the fact that Many of the known binding sites are clustered, to evaluate the P value of obtaining cluster of few binding sites on the same target gene 3 un translated region in the following way: It scans different scores threshold, and calculate for each threshold the number and positions of possible binding sites with score above the threshold. It then gets from a preprocess calculated background matrixes, describe hereinbelow, a P value for each threshold and number and positions of binding sites combination. The output score for each miRNA and target gene pair is the minimal P value, normalized with the number of thresholds trying using Bernoulli distribution. A preference of low P value pairs is made.

As mentioned hereinabove, for each target gene a preprocess calculated background matrixes were build. The matrixes includes rows for each number of miRNA binding site (In the preferred embodiment the matrix include 7 rows for 0 to 6 binding site.), and columns for each different score threshold (In the preferred embodiment the matrix include 5 columns for 5 different threshold). Each matrix cell, corresponding to specific number of binding site and threshold, was set to be the probability to get equal or more binding sites with equal or more score by random sequences with 22 nucleotides length with the same letter distribution as known miRNAs (29.5% T, 24.5% A, 25% G and 21% C). Those probabilities are calculated by running the above procedure for 10000 random sequences. The P value can be estimated as the number of random sequences obeys the matrix cell requirement divided by the total number of random sequences (10000). In the preferred embodiment 2 matrixes are calculated. The P values are of the second matrix are calculated under constrain that at least two of the binding site position are under a heuristically determine constant value. The second matrix values are calculated without this constrain. The TARGET GENE BINDING-SITE DETECTOR uses the second matrix if the binding sites position agree with the constrain, else it uses the first. In an alternative embodiment only one matrix is calculated without any constrain on the binding sites positions.

Test preformed using the TARGET GENE BINDING-SITE DETECTOR showed that all of the known miRNA target genes are found using this algorithm with a P value of less than 0.5%. Running known miRNA against 3400 potential 3' UTR of target genes sequences yield on average 32 target genes for each miRNA with P value less than 0.5%, while background sequences, as well as inverse or complement sequence of known miRNA (which preserve their high order sequence statistics) found, as excepted, on average 17 target genes. This reflects the algorithm performance to detect real target genes with 47% accuracy.

Scoring of all potential binding sites are calculated and P value for obtaining such binding sites list for DICER-CUT SEQUENCE FROM HAIRPIN STRUCTURE and POTENTIAL TARGET GENE SEQUENCE pair is evaluate using the background matrix. In accordance with another preferred embodiment of the present invention, binding sites are searched by a reversed process. Sequences of K (preferably 22) nucleotides of a untranslated regions of a target gene are assessed as potential binding sites. A sequence comparison algorithm, such as BLAST or EDIT DISTANCE varinet, is then used to search elsewhere in the genome for partially or fully complementary sequences which are found in known miRNA oligonucleotides or computationally predicted GAM oligonucleotides. Only complementary sequences, which meet predetermined spatial structure and free energy criteria as described hereinabove, are accepted. Clustered binding sites are strongly preferred and potential binding sites and potential GAM oligonucleotides which occur in evolutionarily conserved genomic sequences are also preferred. Scoring of candidate binding sites takes into account free energy and spatial structure of the binding site complexes, as well as the aforesaid preferences.

Figure 8:
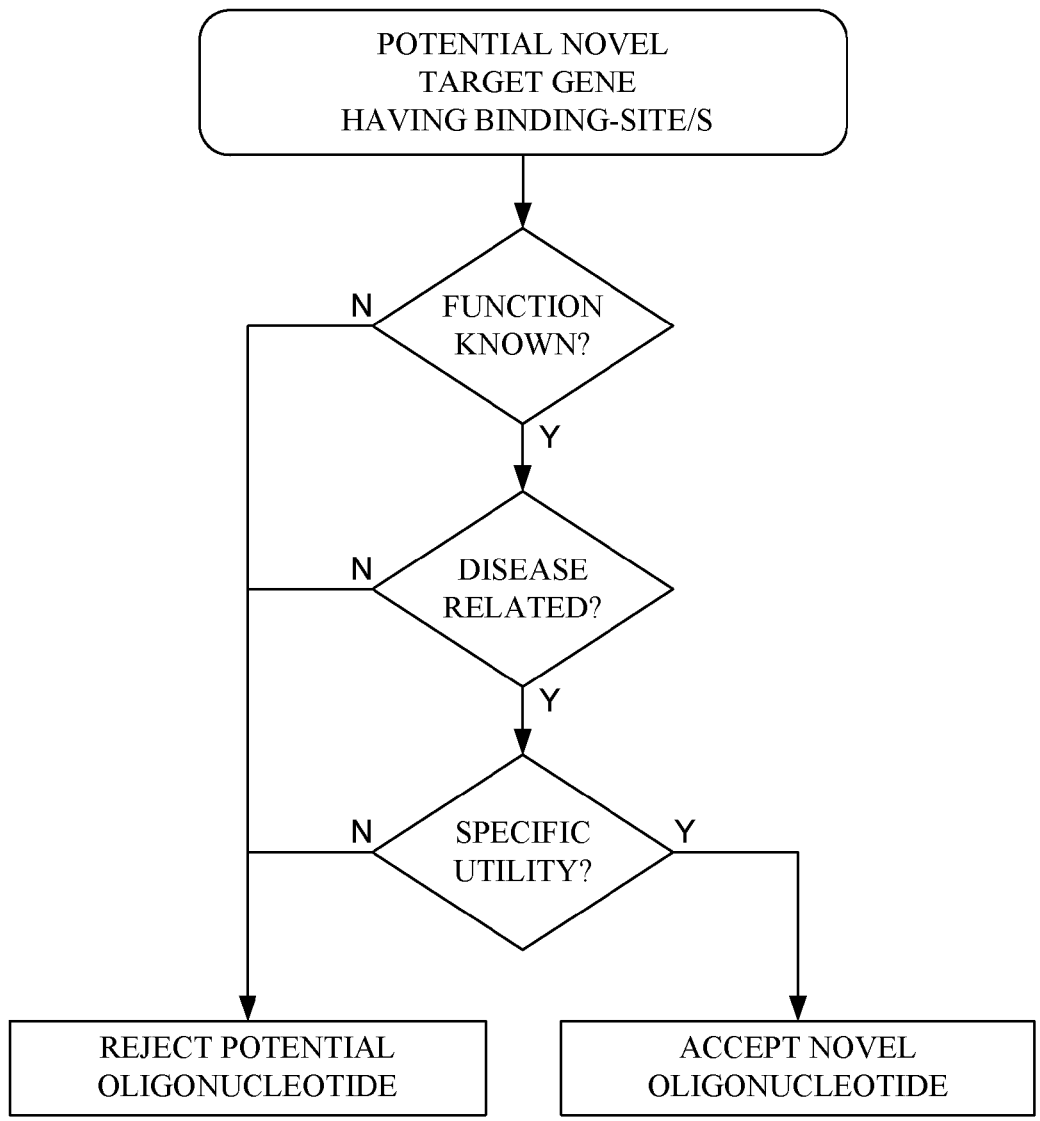
FIG. 8 is a simplified flowchart illustrating operation of a function & utility analyzer constructed and operative in accordance with a preferred embodiment of the present invention.

Reference is now made to FIG. 8 which is a simplified flowchart illustrating a preferred operation of the FUNCTION & UTILITY ANALYZER 120 described hereinabove with reference to FIG. 2. The goal of the FUNCTION & UTILITY ANALYZER 120 is to determine if a potential target gene is in fact a valid clinically useful target gene. Since a potential novel GAM oligonucleotide binding a binding site in the UTR of a target gene is understood to inhibit expression of that target gene, and if that target gene is shown to have a valid clinical utility, then in such a case it follows that the potential novel oligonucleotide itself also has a valid useful function which is the opposite of that of the target gene.

The FUNCTION & UTILITY ANALYZER 120 preferably receives as input a plurality of POTENTIAL NOVEL TARGET GENES HAVING BINDING-SITE/S 144 (FIG. 7A), generated by the TARGET GENE BINDING-SITE DETECTOR 118 (FIG. 2). Each potential oligonucleotide is evaluated as follows: First, the system checks to see if the function of the potential target gene is scientifically well established. Preferably, this can be achieved bioinformatically by searching various published data sources presenting information on known function of proteins. Many such data sources exist and are published as is well known in the art. Next, for those target genes the function of which is scientifically known and is well documented, the system then checks if scientific research data exists which links them to known diseases. For example, a preferred embodiment of the present invention utilizes the OMIM™ (Hamosh et al, 2002) database published by NCBI, which summarizes research publications relating to genes which have been shown to be associated with diseases. Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel oligonucleotides, the target genes of which have passed all three examinations, are accepted as novel oligonucleotide.

Figure 9:
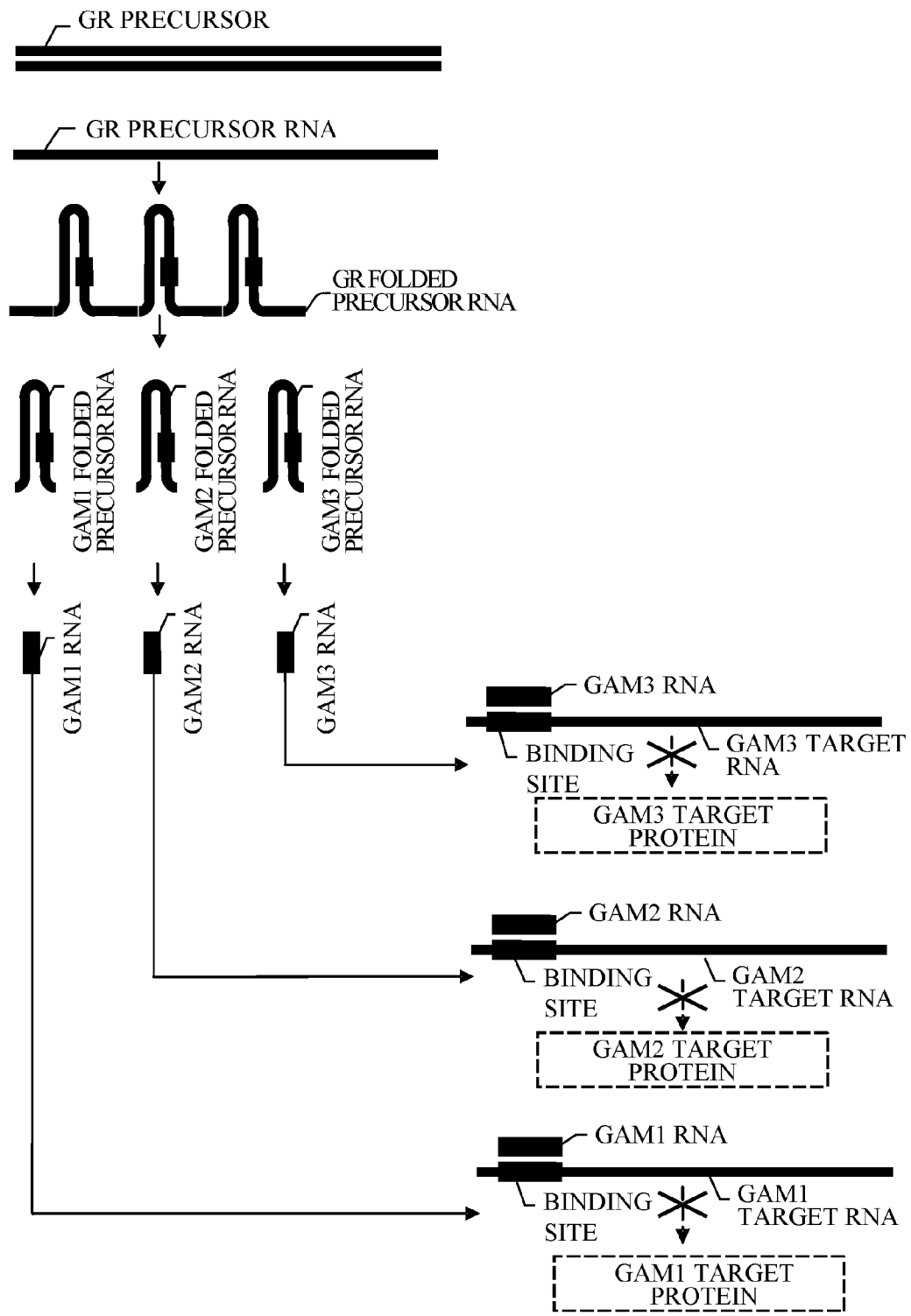
FIG. 9 is a simplified diagram describing a novel bioinformatically detected group of regulatory polynucleotides, referred to here as Genomic Record (GR) polynucleotides, each of which encodes an 'operon-like' cluster of novel miRNA-like oligonucleotides, which in turn modulate expression of one or more target genes.

Reference is now made to FIG. 9, which is a simplified diagram describing each of a plurality of novel bioinformatically detected regulatory polynucleotide referred to here as Genomic Record (GR) polynucleotide, which encodes an 'operon-like' cluster of novel microRNA-like oligonucleotides, each of which in turn modulates expression of at least one target gene; the function and utility of which at least one target gene is known in the art.

GR PRECURSOR is a novel bioinformatically detected regulatory, non protein coding polynucleotide. The method by which GR PRECURSOR is detected is described hereinabove with additional reference to FIGS. 1-9.

GR PRECURSOR is preferably encoded by the bacterial genome and contains cluster of novel bacterial oligonucleotides, which preferably binds to a human target genes or to the bacterium self-genes. Alternatively or additionally, GR PRECURSOR is encoded by the human genome and contains cluster of novel human oligonucleotides, which preferably binds to bacterial target genes or to human self-genes.

GR PRECURSOR encodes GR PRECURSOR RNA, an RNA molecule, typically several hundred to several thousand nucleotides long. GR PRECURSOR RNA folds spatially, forming GR FOLDED PRECURSOR RNA. It is appreciated that GR FOLDED PRECURSOR RNA comprises a plurality of what is known in the art as 'hairpin' structures. These 'hairpin' structures are due to the fact that the nucleotide sequence of GR PRECURSOR RNA comprises a plurality of segments, the first half of each such segment having a nucleotide sequence which is at least a partial or accurate reverse-complement sequence of the second half thereof, as is well known in the art.

GR FOLDED PRECURSOR RNA is naturally processed by cellular enzymatic activity into a plurality of separate GAM precursor RNAs, herein schematically represented by GAM1 FOLDED PRECURSOR RNA through GAM3 FOLDED PRECURSOR RNA, each of which GAM folded precursor RNAs being a hairpin shaped RNA segment, corresponding to GAM FOLDED PRECURSOR RNA of FIG. 1.

The above mentioned GAM folded precursor RNAs are diced by DICER COMPLEX of FIG. 1, yielding respective short RNA segments of about 22 nucleotides in length, schematically represented by GAM1 RNA through GAM3 RNA, each of which GAM RNAs corresponding to GAM RNA of FIG. 1. GAM1 RNA, GAM2 RNA and GAM3 RNA, each bind complementarily to binding sites located in untranslated regions of respective target genes, designated GAM1 TARGET RNA, GAM2 TARGET RNA and GAM3 TARGET RNA, respectively, which target binding site corresponds to a target binding site such as BINDING SITE I, BINDING SITE II or BINDING SITE III of FIG. 1. This binding inhibits translation of the respective target proteins designated GAM1 TARGET PROTEIN, GAM2 TARGET PROTEIN and GAM3 TARGET PROTEIN respectively.

It is appreciated that specific functions, and accordingly utilities of GR polynucleotide are correlated with and may be deduced from the identity of the target genes, which are inhibited by GAM RNAs comprised in the 'operon-like' cluster of GR polynucleotide, schematically represented by GAM1 TARGET PROTEIN through GAM3 TARGET PROTEIN. The function of these target genes is elaborated in Table 8, hereby incorporated herein.

Figure 10:
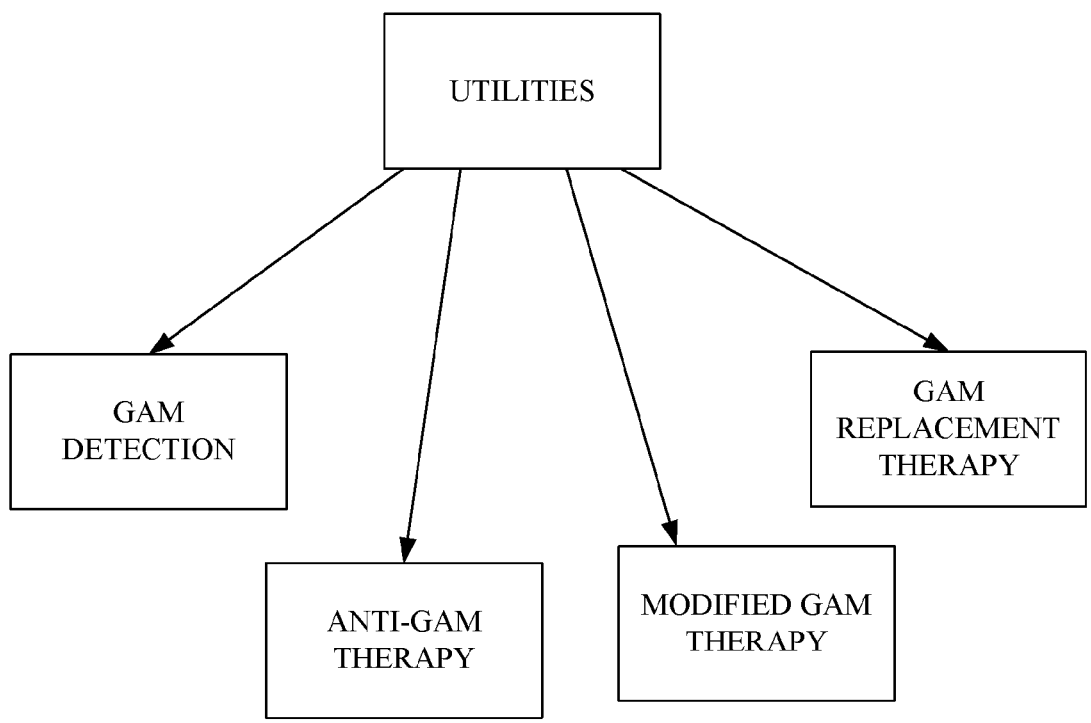
FIG. 10 is a block diagram illustrating different utilities of novel oligonucleotides and novel operon-like polynucleotides, both of the present invention.

Reference is now made to FIG. 10 which is a block diagram illustrating different utilities of oligonucleotide of the novel group of oligonucleotides of the present invention referred to here as GAM oligonucleotides and GR polynucleotides. The present invention discloses a first plurality of novel oligonucleotides referred to here as GAM oligonucleotides and a second plurality of operon-like polynucleotides referred to here as GR polynucleotides, each of the GR polynucleotide encoding a plurality of GAM oligonucleotides. The present invention further discloses a very large number of known target genes, which are bound by, and the expression of which is modulated by each of the novel oligonucleotides of the present invention. Published scientific data referenced by the present invention provides specific, substantial, and credible evidence that the above mentioned target genes modulated by novel oligonucleotides of the present invention, are associated with various diseases. Specific novel oligonucleotides of the present invention, target genes thereof and diseases associated therewith, are described hereinbelow with reference to Tables 1 through 10. It is therefore appreciated that a function of GAM oligonucleotides and GR polynucleotides of the present invention is modulation of expression of target genes related to known bacterial diseases, and that therefore utilities of novel oligonucleotides of the present invention include diagnosis and treatment of the above mentioned diseases.

FIG. 10 describes various types of diagnostic and therapeutic utilities of novel oligonucleotides of the present invention. A utility of novel oligonucleotide of the present invention is detection of GAM oligonucleotides and of GR polynucleotides. It is appreciated that since GAM oligonucleotides and GR polynucleotides modulate expression of disease related target genes, that detection of expression of GAM oligonucleotides in clinical scenarios associated with said bacterial diseases is a specific, substantial and credible utility. Diagnosis of novel oligonucleotides of the present invention may preferably be implemented by RNA expression detection techniques, including but not limited to biochips, as is well known in the art. Diagnosis of expression of oligonucleotides of the present invention may be useful for research purposes, in order to further understand the connection between the novel oligonucleotides of the present invention and the above mentioned related bacterial diseases, for disease diagnosis and prevention purposes, and for monitoring disease progress.

Another utility of novel oligonucleotides of the present invention is anti-GAM therapy, a mode of therapy which allows up regulation of a bacterial disease-related target gene of a novel GAM oligonucleotide of the present invention, by lowering levels of the novel GAM oligonucleotide which naturally inhibits expression of that target gene. This mode of therapy is particularly useful with respect to target genes which have been shown to be under-expressed in association with a specific bacterial disease. Anti-GAM therapy is further discussed hereinbelow with reference to FIGS. 11A and 11B.

A further utility of novel oligonucleotides of the present invention is GAM replacement therapy, a mode of therapy which achieves down regulation of a bacterial disease related target gene of a novel GAM oligonucleotide of the present invention, by raising levels of the GAM which naturally inhibits expression of that target gene. This mode of therapy is particularly useful with respect to target genes which have been shown to be over-expressed in association with a specific bacterial disease. GAM replacement therapy involves introduction of supplementary GAM products into a cell, or stimulation of a cell to produce excess GAM products. GAM replacement therapy may preferably be achieved by transfecting cells with an artificial DNA molecule encoding a GAM which causes the cells to produce the GAM product, as is well known in the art.

Yet a further utility of novel oligonucleotides of the present invention is modified GAM therapy. Disease conditions are likely to exist, in which a mutation in a binding site of a GAM RNA prevents natural GAM RNA to effectively bind inhibit a bacterial disease related target gene, causing up regulation of that target gene, and thereby contributing to the disease pathology. In such conditions, a modified GAM oligonucleotides is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM which causes the cells to produce the modified GAM product, as is well known in the art.

Figure 11A:
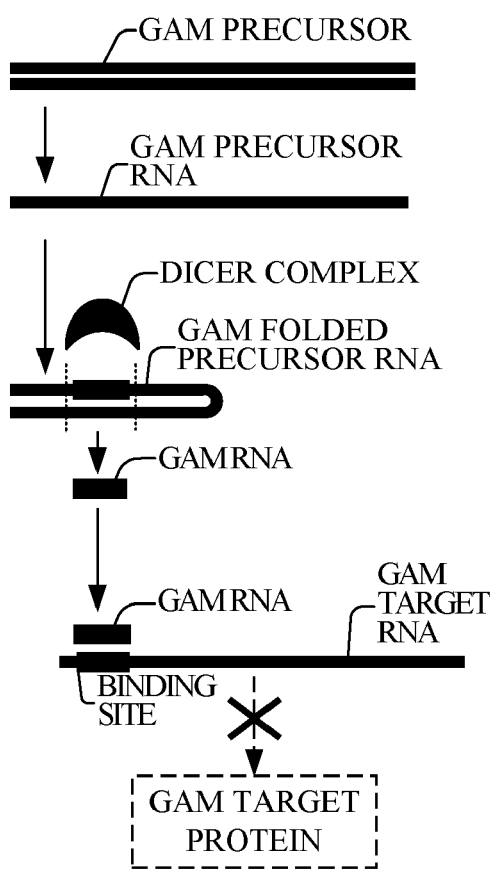
FIGS. 11A and 11B are simplified diagrams, which when taken together illustrate a mode of oligonucleotide therapy applicable to novel oligonucleotides of the present invention.
Figure 11B:
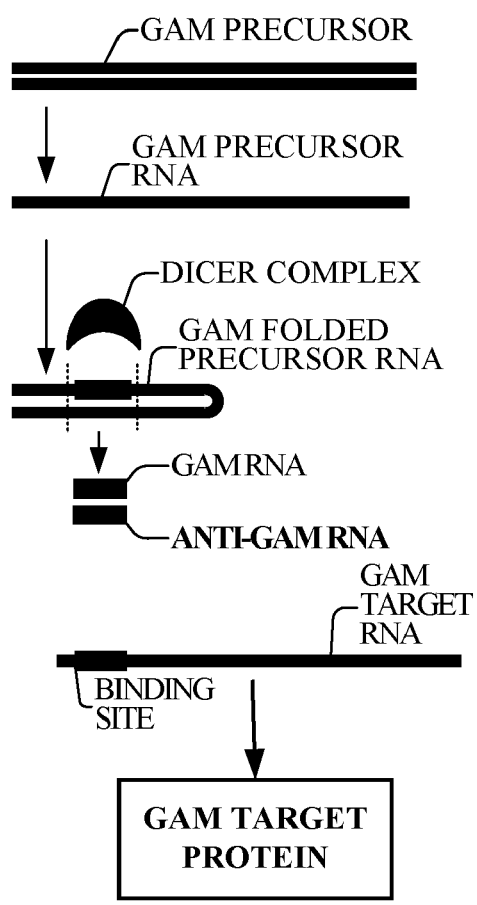

Reference is now made to FIGS. 11A and 11B, simplified diagrams which when taken together illustrate anti-GAM therapy mentioned hereinabove with reference to FIG. 10. A utility of novel GAMs of the present invention is anti-GAM therapy, a mode of therapy which allows up regulation of a bacterial disease-related target gene of a novel GAM of the present invention, by lowering levels of the novel GAM which naturally inhibits expression of that target gene. FIG. 11A shows a normal GAM inhibiting translation of a target gene by binding of GAM RNA to a BINDING SITE found in an untranslated region of GAM TARGET RNA, as described hereinabove with reference to FIG. 1.

FIG. 11B shows an example of anti-GAM therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM therapy is particularly useful with respect to target genes which have been shown to be under-expressed in association with a specific bacterial disease.

Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly up regulate translation of target proteins.

Figure 12A:
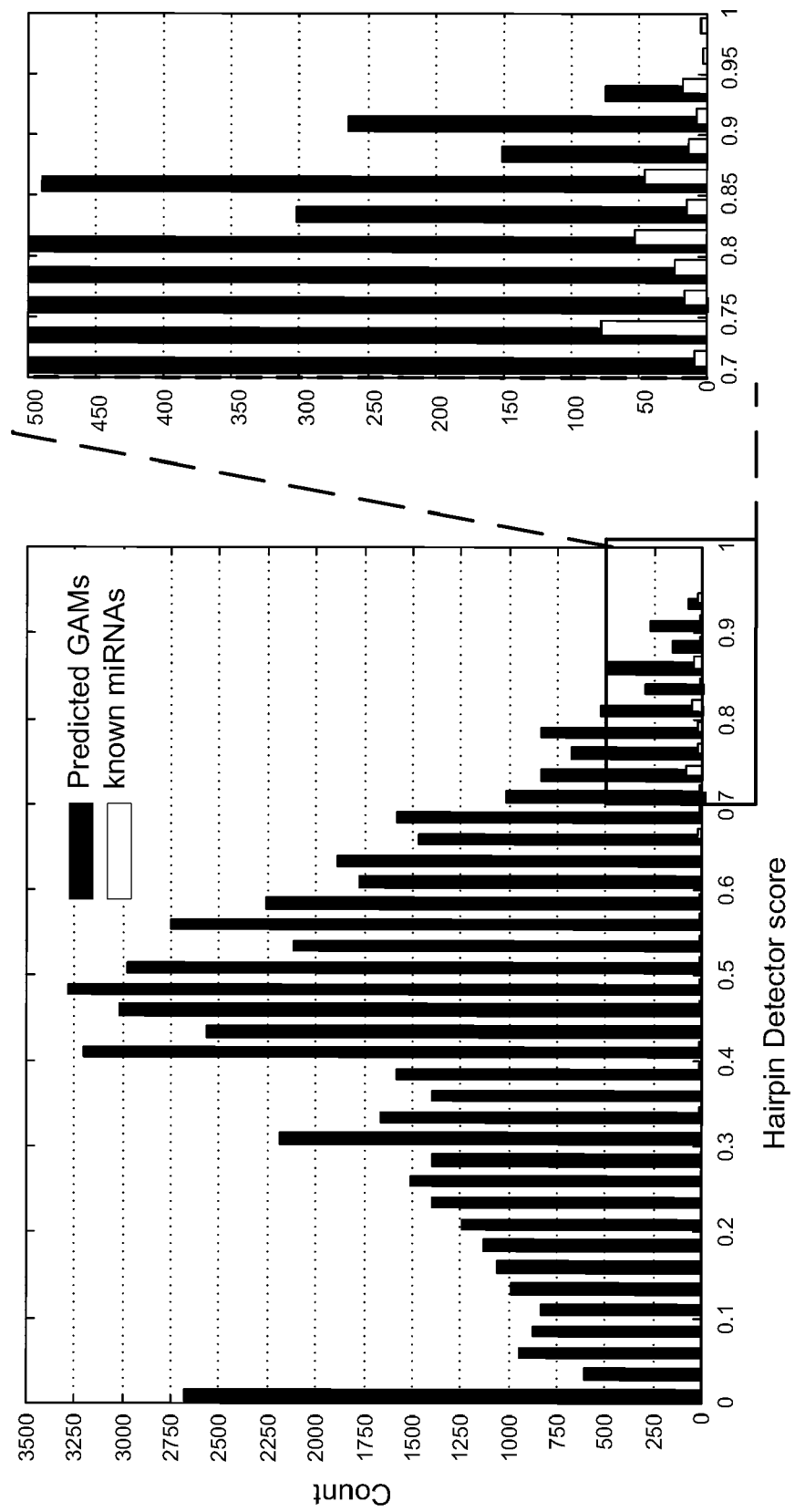
FIG. 12A is a histogram representing the distribution of known miRNA oligonucleotides and that of predicted miRNA-like hairpin structures extracted from expressed genome sequences with respect to their hairpin detector score.

Reference is now made to FIG. 12A, which is a histogram representing the distribution of known miRNA oligonucleotides and that of hairpin structures extracted from expressed human genome sequences with respect to their HAIRPIN DETECTOR score (this analysis preferably uses the previous version of the Hairpin Detector program). The known miRNA oligonucleotides set is taken from RFAM database, Release 2.1 and includes 440 miRNA oligonucleotides from H. sapienas, M. musculus, C. elegans, C. brigassae and D. melanogaster. Folding of expressed genome sequences taken from public databases of ESTs (Unigene-NCBI and TIGR) identified 342,882 hairpin structures. ~154,000 out of the 342,882 hairpin structures did not pass the filter of being identified as hairpins in several secondary structure folding versions of the given genomic sequence, as described hereinabove with reference to FIG. 5B, and hence did not receive a Hairpin detector score. Furthermore, ~133,000 hairpin structures did not pass the filter of minimum score of the DICER-CUT LOCATION DETECTOR 116 (FIG. 2) (those ~287,000 hairpin structures are not represented in the histogram). Hairpin structures are considered as miRNA-like precursor oligonucleotides here referred to as GAM precursor, if their Hairpin detector score is above 0.3. Thus, the GAM precursor set is comprised of ~40,000 hairpin structures, of those ~5100 received a high Hairpin detector score (>=0.7). These are much higher numbers than those of the known miRNA oligonucleotides and of the upper bound of ~255 human miRNA oligonucleotides, estimated by Bartel et al. (Science, 299, 1540, March 2003). Of the reference set that pass the above filter (408/440), 284 (69%) received a high Hairpin detector score (>=0.7).

Reference is now made to FIG. 12B, which is a table summarizing laboratory validation results that validate efficacy of the BIOINFORMATIC OLIGONUCLEOTIDE DETECTION ENGINE 100 (FIG. 2). In order to assess efficacy of the BIOINFORMATIC OLIGONUCLEOTIDE DETECTION ENGINE 100, novel oligonucleotides predicted thereby are preferably filtered using the scores of HAIRPIN DETECTOR 114 (FIG. 2) and DICER-CUT LOCATION DETECTOR 116 (FIG. 2) as follows: covering 85% (second column) of published hairpin our algorithm enable to filter 95% of background (third column), leaving only dozens of predicted hairpins with relatively high probability of being a real hairpin carrying a 'diced' miRNA for lab validation.

Group A (selected for the present invention, first column): The score of the HAIRPIN-DETECTOR is above 0, the overall score of the two-phased predictor is above 0.55, and the score of the second phase of the two-phased predictor is above 0.75, or the score of the EDIT-DISTANCE predictor is equal or above 17. In this group, one Dicer cut location is predicted for each hairpin.

Sample of novel bioinformatically predicted human GAMs are sent to the laboratory for validation (fourth column), and the number (fifth column) and percent (sixth column) of successful validation of predicted human GAM is noted for each of the groups, as well as overall (bottom line). The information about the above lab validation is based on previous patents group selections, there is a high correlation between the old group A predicted hairpin and the present one indicate that the update results should be approximately the same or better, due to improvement in the predictions.

It is appreciated that the present invention comprises 6444 novel GAM oligonucleotides, which fall into group A, and that the BIOINFORMATIC OLIGONUCLEOTIDE DETECTION ENGINE 100 (FIG. 2) is substantiated by a group of 37 novel human GAM oligonucleotides validated by laboratory means, out of 101 human GAM oligonucleotides which were tested in the lab, resulting in validation of an overall 31% accuracy. The selected group demonstrated 37% accuracy. Pictures of test-results of specific human GAM oligonucleotides as well as the methodology used for validating the expression of predicted oligonucleotides are elaborated hereinbelow with reference to FIG. 13.

It is further appreciated that failure to detect a predicted oligonucleotide in the lab does not necessarily indicate a mistaken bioinformatic prediction. Rather, it may be due to technical sensitivity limitation of the lab test, or because the predicted oligonucleotides are not expressed in the tissue examined, or at the development phase tested.

It is still further appreciated that in general these findings are in agreement with the expected bioinformatic accuracy, as describe hereinabove with reference to FIG. 6B: assuming 80% accuracy of the HAIRPIN DETECTOR 114 and 80% accuracy of the DICER-CUT LOCATION DETECTOR 116 and 80% accuracy of the lab validation, this would result in 50% overall accuracy of the predicted oligonucleotide validated in the lab.

Figure 13A:
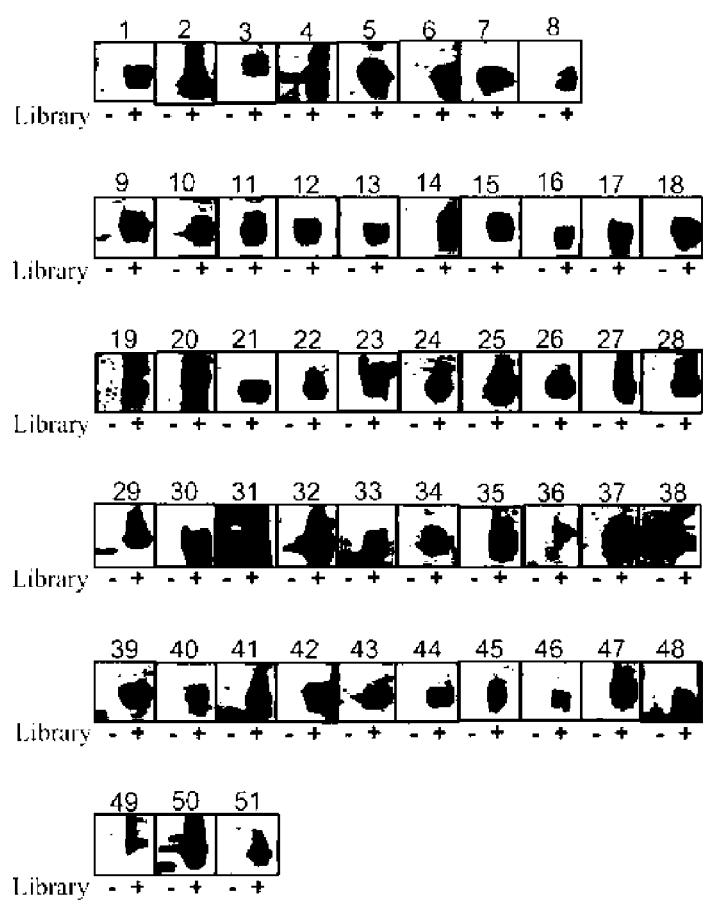

Reference is now made to FIG. 13A which is a picture of laboratory results validating the expression of 43 novel human GAM oligonucleotides detected by the BIOINFORMATIC OLIGONUCLEOTIDE DETECTION ENGINE 100 (FIG. 2).

Reference is now made to FIG. 13A and FIG. 13B which are pictures and a summary table of laboratory results validating the expression of 43 novel human GAM oligonucleotides detected by the BIOINFORMATIC OLIGONUCLEOTIDE DETECTION ENGINE 100. In each row in FIG. 13A, pictures of several oligonucleotides validated by hybridization of Polymerase Chain Reaction (PCR)-product southern-blots, are provided, each corresponding to a specific GAM oligonucleotide, as elaborated hereinbelow. To test our validation method, we used a reference set of 8 known human miRNA oligonucleotides, as a blind test to our laboratory. These PCR-product hybridization pictures are designated 1 through 8 for the reference set known miRNA oligonucleotides; and 9 through 51 for predicted GAM oligonucleotides.

In each PCR hybridization picture, 2 lanes are seen: the test lane, designated "+" and the control lane, designated "−". The control reaction contained all the components of the test reaction except library template. For convenience of viewing the results, all PCR-product hybridization pictures of FIG. 22A have been shrunk ×4 vertically. It is appreciated that for each of the tested GAM oligonucleotides a clear hybridization band appears in the test ("+") lane, but not in the control ("−") lane.

Specifically, FIG. 13A shows pictures of PCR-product hybridization validation by southern-blot, the methodology of which is described hereinbelow, to the following novel human GAM oligonucleotides (RosettaGenomics Ltd. Nomenclature, 'A' and 'B' referred to the Dicer Cut Location as described hereinbelow with reference to the description of large tables:

(1) hsa-MIR-21; (2) hsa-MIR-27b; (3) hsa-MIR-186; (4) hsa-MIR-93; (5) hsa-MIR-26a; (6) hsa-MIR-191; (7) hsa-MIR-31; (8) hsa-MIR-92; (9) GAM3418-A (later published by other researchers as hsa-MIR23); (10) GAM4426-A; (11) GAM281-A; (12) GAM7553-A; (13) GAM5385-A; (14) GAM2608-A; (15) GAM1032-A; (16) GAM3431-A; (17) GAM7933-A; (18) GAM3298-A; (19) GAM7080-A; (20) GAM895-A; (21) GAM3770.1; (22) GAM337162-A; (23) GAM 8678-A; (24) GAM2033-A; (25) GAM7776-A; (26) GAM8145-A; (27) GAM25-A; (28) GAM7352.1; (29) GAM337624-A; (30) GAM1479-A; (31) GAM2270-A; (32) GAM7591-A; (33) GAM8285-A; (34) GAM6773-A; (35) GAM336818-A; (36) GAM336487-A; (37) GAM337620-A; (38) GAM336809-A; (39) GAM5346-A; (40) GAM8554-A; (41) GAM2071-A; (42) GAM7957-A; (43) GAM391-A; (44) GAM6633-A; (45) GAM19; (46) GAM8358-A; (47) GAM3229-A; an) GAM 7052-A; (49) GAM3027-A; (50) GAM21 and (51) GAM oligonucleotide similar to mmu-MIR-30e.

The next validated GAM oligonucleotides are highly similar or identical to known mouse-miRNA oligonucleotides: GAM3027-A, similar to mmu-MIR-29c; GAM21, similar to mmu-MIR-130b; and GAM oligonucleotide which is highly similar to mmu-MIR-30e (picture number 51). In addition to the PCR—product hybridization detection, the following GAMs were also cloned and sequenced: GAM3418-A, GAM5385-A, GAM1032-A, GAM3298-A, GAM7080-A, GAM1338-A, GAM7776-A, GAM25-A, GAM337624-A, GAM1479-A, GAM6773-A, GAM336818-A, GAM336487-A, GAM337620-A, GAM336809-A, GAM3027-A, GAM21, and GAM oligonucleotide similar to mmu-MIR-30e (picture number 51). Furthermore, the following GAM oligonucleotides were sequenced directly from the ligation reaction by the method described hereinbelow under LIGATION-PCR DIAGNOSTIC METHOD: GAM4426-A, GAM7553-A, GAM2270-A, and GAM7591-A.

In order to validate the expression of predicted novel GAMs and assuming that these novel GAM oligonucleotides are probably expressed at low concentrations, a PCR product cloning approach was set up through the following strategy: two types of cDNA libraries designated "One tailed" and "Ligation" were prepared from frozen HeLa S100 extract (4c Biotech, Belgium) size fractionated RNA. Essentially, Total S100 RNA was prepared through an SDS-Proteinase K incubation followed by an acid Phenol-Chloroform purification and Isopropanol precipitation. Alternatively, total HeLa RNA was also used as starting material for these libraries.

Fractionation was done by loading up to 500 g per YM100 Amicon Microcon column (Millipore) followed by a 500 g centrifugation for 40 minutes at 4° C. Flow through "YM100" RNA consisting of about of the total RNA was used for library preparation or fractionated further by loading onto a YM30 Amicon Microcon column (Millipore) followed by a 13,500 g centrifugation for 25 minutes at 4° C. Flowthrough "YM30" was used for library preparation as is and consists of less than 0.5% of total RNA. For the both the "ligation" and the "One-tailed" libraries, RNA was dephosphorylated and ligated to an RNA (lowercase)-DNA (UPPERCASE) hybrid 5-phosphorylated, 3 idT blocked 3-adapter (5-P-uuuAACCGCATC-CTTCTC-idT-3 (SEQ ID No: 59888) Dharmacon #P-002045-01-05) (as elaborated in Elbashir et al., Genes Dev. 15:188-200 (2001)) resulting in ligation only of RNase III type cleavage products. 3-Ligated RNA was excised and purified from a half 6%, half 13% polyacrylamide gel to remove excess adapter with a Nanosep 0.2M centrifugal device (Pall) according to instructions, and precipitated with glycogen and 3 volumes of Ethanol. Pellet was resuspended in a minimal volume of water.

For the "ligation" library a DNA (UPPERCASE)-RNA (lowercase) hybrid 5-adapter (5-TACTAATACGACTCAC-Taaa-3 (SEQ ID No: 59889) Dharmacon #P-002046-01-05) was ligated to the 3-adapted RNA, reverse transcribed with "EcoRI-RT": (5-GACTAGCTGGAATTCAAGGATGCG-GTTAAA-3)SEQ ID No: 59890, PCR amplified with two external primers essentially as in Elbashir et al 2001 except that primers were "EcoRI-RT" and "PstI Fwd" (5-CAGC-CAACGCTGCAGATACGACTCAC TAAA-3). (SEQ ID No: 59891). This PCR product was used as a template for a second round of PCR with one hemispecific and one external primer or with two hemispecific primers.

For the "One tailed" library the 3-Adapted RNA was annealed to 20 pmol primer "EcoRI RT" by heating to 70° C.

and cooling 0.1° C./sec to 30° C. and then reverse transcribed with Superscript II RT (According to instructions, Invitrogen) in a 20l volume for 10 alternating 5 minute cycles of 37° C. and 45° C. Subsequently, RNA was digested with 1l 2M NaOH, 2 mM EDTA at 65° C. for 10 minutes. cDNA was loaded on a polyacrylamide gel, excised and gel-purified from excess primer as above (invisible, judged by primer run alongside) and resuspended in 13l of water. Purified cDNA was then oligo-dC tailed with 400 U of recombinant terminal transferase (Roche molecular biochemicals), 1l 100M dCTP, 1l 15 mM CoCl2, and 4l reaction buffer, to a final volume of 20l for 15 minutes at 37 C. Reaction was stopped with 2l 0.2M EDTA and 15l 3M NaOAc pH 5.2. Volume was adjusted to 150l with water, Phenol: Bromochloropropane 10:1 extracted and subsequently precipitated with glycogen and 3 volumes of Ethanol. C-tailed cDNA was used as a template for PCR with the external primers "T3-PstBsg(G/I)18" (5-AATTAACCCTCACTAA AGGCTGCAGGTGCAG-GIGGGIIGGGIIGGGIIGN-3 (SEQ ID No: 59892 where I stands for Inosine and N for any of the 4 possible deoxynucleotides), and with "EcoRI Nested" (5-GGAATTCAAGGAT-GCGGTTA-3) (SEQ ID No: 59893). This PCR product was used as a template for a second round of PCR with one hemispecific and one external primer or with two hemispecific primers.

Hemispecific primers were constructed for each predicted GAM RNA oligonucleotide by an in-house program designed to choose about half of the 5 or 3 sequence of the GAM RNA corresponding to a TM of about 30-34° C. constrained by an optimized 3 clamp, appended to the cloning adapter sequence (for "One-tailed" libraries 5-GGN-NGGGNNG (SEQ ID No: 59894on the 5 end of the GAM RNA, or TTTAACCGCATC-3 (SEQ ID No: 59895 on the 3 end of the GAM RNA. For "Ligation" libraries the same 3 adapter and 5- CGACTCACTAAA (SEQ ID No: 59896 ) on the 5 end). Consequently, a fully complementary primer of a TM higher than 60 C was created covering only one half of the GAM RNA sequence permitting the unbiased elucidation by sequencing of the other half.

CONFIRMATION OF GAM OLIGONUCLEOTIDE SEQUENCE AUTHENTICITY OF PCR PRODUCTS:

SOUTHERN BLOT: PCR-product sequences were confirmed by southern blot (Southern E. M., Biotechnology, 1992, 24:122-39 (1975)) and hybridization with DNA oligonucleotide probes synthesized as complimentary (antisense) to predicted GAM RNA oligonucleotides. Gels were transferred onto a Biodyne PLUS 0.45m, (Pall) positively charged nylon membrane and UV cross-linked. Hybridization was performed overnight with DIG-labeled probes at 420 C in DIG Easy-Hyb buffer (Roche). Membranes were washed twice with 2×SSC and 0.1% SDS for 10 minutes at 420 C and then washed twice with 0.5×SSC and 0.1% SDS for 5 min at 420 C. The membrane was then developed by using a DIG luminescent detection kit (Roche) using anti-DIG and CSPD reaction, according to the manufacturer's protocol. All probes were prepared according to the manufacturers (Roche Molecular Biochemicals) protocols: Digoxigenin (DIG) labeled antisense transcripts was prepared from purified PCR products using a DIG RNA labeling kit with T3 RNA polymerase. DIG labeled PCR was prepared by using a DIG PCR labeling kit. 3-DIG-tailed oligo ssDNA antisense probes, containing DIG-dUTP and dATP at an average tail length of 50 nucleotides were prepared from 100 pmole oligonucleotides with the DIG Oligonucleotide Labeling Kit.

CLONE-SEQUENCING: PCR products were inserted into pGEM-T (Promega) or pTZ57/T (MBI Fermentas), heat-shock transformed into competent JM109 E. coli (Promega) and sown on LB-Ampiccilin plates with IPTG and Xgal. White and light-blue colonies were transferred to duplicate gridded plates, one of which was blotted onto a membrane (Biodyne Plus, Pall) for hybridization with DIG tailed oligo probes (according to instructions, Roche) complimentary to the expected GAM. Plasmid DNA from positive colonies was sequenced.

LIGATION-PCR DIAGNOSTIC METHOD: To further validate predicted GAM PCR product sequence derived from hemi-primers, a PCR based diagnostic technique was devised to amplify only those products containing also at least two additional nucleotides of the non hemi-primer defined part of the predicted GAM RNA oligonucleotide. In essence, a diagnostic primer was designed so that its 3 end, which is the specificity determining side, was identical to the desired GAM RNA oligonucleotide, 2-10 nucleotides (typically 4-7, chosen for maximum specificity) further into its 3 end than the nucleotide stretch primed by the hemi-primer. The hemi-primer PCR product was first ligated into a T-cloning vector (pTZ57/T or pGEM-T) as described hereinabove. The ligation reaction mixture was used as template for the diagnostic PCR under strict annealing conditions with the new diagnostic primer in conjunction with a general plasmid-homologous primer, resulting in a distinct ~200 base-pair product. This PCR product can be directly sequenced, permitting the elucidation of the remaining nucleotides up to the 3 of the mature GAM RNA oligonucleotide adjacent to the 3 adapter. Alternatively, following analysis of the diagnostic PCR reaction on an agarose gel, positive ligation reactions (containing a band of the expected size) were transformed into E. coli. Using this same diagnostic technique and as an alternative to screening by Southern-blot colonyhybridization, transformed bacterial colonies were screened by colony-PCR (Gussow, D. and Clackson, T, Nucleic Acids Res. 17: 4000 (1989)) prior to plasmid purification and sequencing.

Reference is now made to FIG. 13B which is a table summarizing laboratory results which validate the expression of 8 known human miRNA oligonucleotides and 43 novel GAM oligonucleotides detected by the BIOINFORMATIC OLIGONUCLEOTIDE DETECTION ENGINE 100. The table gives additional information on the above GAM oligonucleotides and contains the following fields: NUMBER: refers to the hybridization picture number of FIG. 13A; NAME: indicates the known MIR name for the reference set, or the GAM's name as given by RosettaGenomics nomenclature method; SEQUENCE: 5' to 3' sequence of the mature, 'diced' oligonucleotide; SEQUENCED: '+' indicates the additional validation of the GAM RNA sequence by sequencing procedure as described hereinabove with reference to FIG. 13A.

Figures 14A, 14B, 14C:
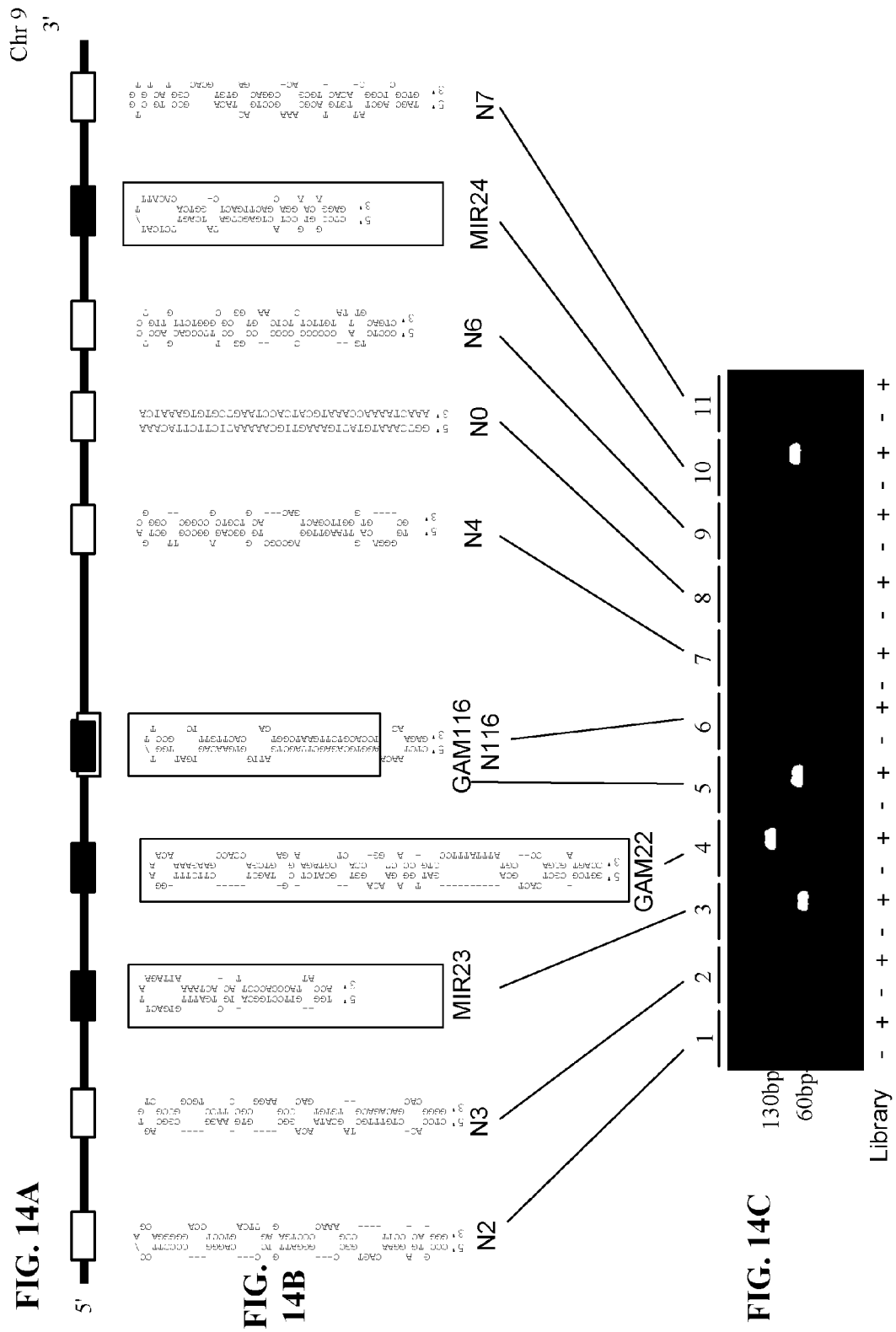
FIG. 14A is a schematic representation of an "operon-like" cluster of novel human hairpin sequences detected bioinformatically by a bioinformatic oligonucleotide detection engine constructed and operative in accordance with a preferred embodiment of the present invention, and non-GAM hairpin useful as negative controls thereto.
FIG. 14B is a schematic representation of secondary folding of hairpins of the operon-like cluster of FIG. 14A. The following hairpins are shown in FIG. 14B: MIR24 (SEQ ID NO: 59885), MIR23 (SEQ ID NO: 59878), GA22 (SEQ ID NO: 59879) and GA116 (SEQ ID NO: 59881), N2 (SEQ ID NO: 59876), 3 (SEQ ID NO: 59877), N116 (SEQ ID NO: 59880), N4 (SEQ ID NO: 59882), N6 (SEQ ID NO: 59884), N7 (SEQ ID NO: 59886), and N0 (SEQ ID NO: 59883)
FIG. 14C is a picture of laboratory results demonstrating expression of novel oligonucleotides of FIGS. 14A and 14B, and lack of expression of the negative controls, thereby validating efficacy of bioinformatic detection of GAM oligonucleotides and GR polynycleotides detected by a bioinformatic oligonucleotide detection engine, constructed and operative in accordance with a preferred embodiment of the present invention.

Reference is now made to FIG. 14A, which is a schematic representation of a novel human GR polynucleotide herein designated GR12731 (RosettaGenomics Ltd. nomenclature), located on chromosome 9, comprising 2 known human MIR oligonucleotides—MIR24 and MIR23, and 2 novel GAM oligonucleotides, herein designated GAM22 and GAM116, all marked by solid black boxes. FIG. 14A also schematically illustrates 6 non-GAM hairpin sequences, and one non-hairpin sequence, all marked by white boxes, and serving as negative controls. By "non-GAM hairpin sequences" is meant sequences of a similar length to known MIR PRECURSOR sequences, which form hairpin secondary folding pattern similar to MIR PRECURSOR hairpins, and yet which are assessed by the BIOINFORMATIC OLIGONUCLEOTIDE DETECTION ENGINE 100 not to be valid GAM PRECURSOR hairpins. It is appreciated that FIG. 14A is a simplified schematic representation, reflecting only the order in which the segments of interest appear relative to one another, and not a proportional distance between the segments.

Reference is now made to FIG. 14B, which is a schematic representation of secondary folding of each of the MIRs and GAMS of GR GR12731 MIR24 (SEQ ID NO: 59885), MIR23 (SEQ ID NO: 59878), GAM22 (SEQ ID NO:59879) and GAM116 (SEQ ID NO: 59881), and of the negative control non-GAM hairpins, herein designated N2 (SEQ ID NO: 59876), N3 (SEQ ID NO: 59877), N116 (SEQ ID NO: 59880), N4 (SEQ ID NO: 59882), N6 (SEQ ID NO: 59884) and N7 (SEQ ID NO: 59886). N0 (SEQ ID NO: 59883) is a non-hairpin control, of a similar length to that of known MIR PRECURSOR hairpins. It is appreciated that the negative controls are situated adjacent to and in between real MIR genes and GAM predicted oligonucleotide and demonstrates similar secondary folding patterns to that of known MIRs and GAMS.

Reference is now made to FIG. 14C, which is a picture of laboratory results of a PCR test upon a YM100 size-fractionated "ligation"-library, utilizing a set of specific primer pairs located directly inside the boundaries of the hairpins. Due to the nature of the library the only PCR amplifiable products can result from RNaseIII type enzyme cleaved RNA, as expected for legitimate hairpin precursors presumed to be produced by DROSHA (Lee et al, Nature 425 415-419, 2003). FIG. 14C demonstrates expression of hairpin precursors of known MIR oligonucleotides MIRhsa-23 and MIRhsa-24, and of novel bioinformatically detected GAM22 and GAM116 hairpins predicted bioinformatically by a system constructed and operative in accordance with a preferred embodiment of the present invention. FIG. 14C also shows that none of the 7 controls (6 hairpins designated N2, N3, N23, N4, N6 and N7 and 1 non-hairpin sequence designated N0) were expressed. N116 is a negative control sequence partially overlapping GAM116.

In the picture, test lanes including template are designated "+" and the control lane is designated "−". The control reaction contained all the components of the test reaction except library template. It is appreciated that for each of the tested hairpins, a clear PCR band appears in the test ("+") lane, but not in the control ("−") lane.

FIGS. 14A through 14C, when taken together validate the efficacy of the bioinformatic oligonucleotide detection engine in: (a) detecting known MIR oligonucleotides; (b) detecting novel GAM PRECURSOR hairpins which are found adjacent to these MIR oligonucleotides, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM oligonucleotides since hairpins are highly abundant in the genome. Other MIR prediction programs have not been able to address this challenge successfully.

Reference is now made to FIG. 15A which is an annotated sequence of an EST comprising a novel GAM oligonucleotides detected by the oligonucleotide detection system of the present invention. FIG. 15A shows the nucleotide sequence of a known human non-protein coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA oligonucleotide, identified as hsa-MIR98, and of one novel GAM oligonucleotide referred to here as GAM25, detected by the BIOINFORMATIC OLIGONUCLEOTIDE DETECTION ENGINE 100 (FIG. 2) of the present invention.

The whole sequence presented FIG. 15A is part of EST72223 (SEQ ID No. 59887). This sequence includes, among others, the four marked sequences: The sequence of the miRNA-98 hairpin in bold, the sequence of the mature miRNA-98 in bold and underlined, the sequence of the GAM25 hairpin in bold and the sequence of the mature miRNA of GAM25 in bold and underlined.

The sequences of the precursors of the known MIR98 and of the predicted GAM25 precursors are marked in bold, the sequences of the established miRNA 98 and of the predicted miRNA-like oligonucleotide GAM25 are underlined.

Figure 15C:
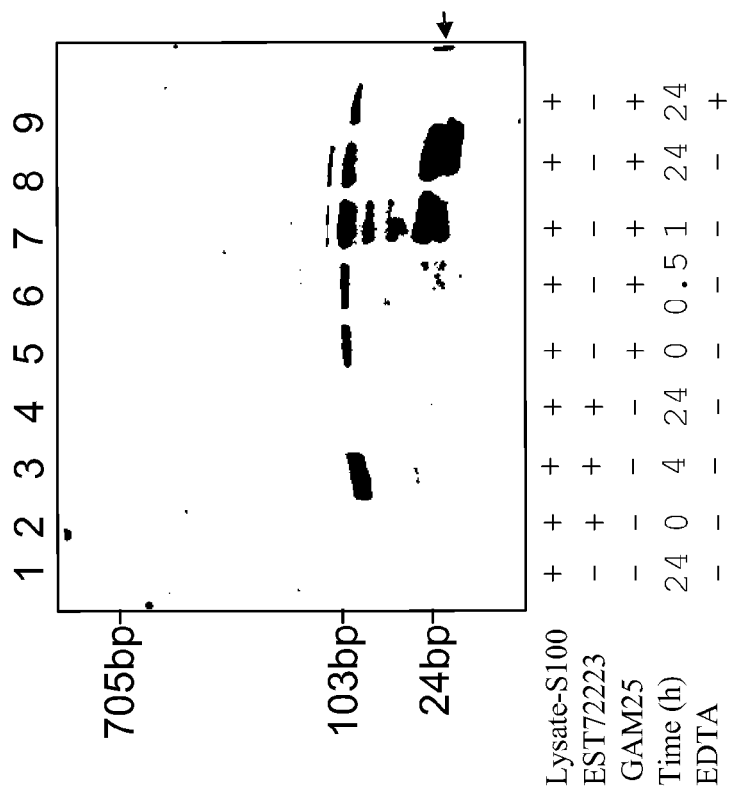
Figure 15D:
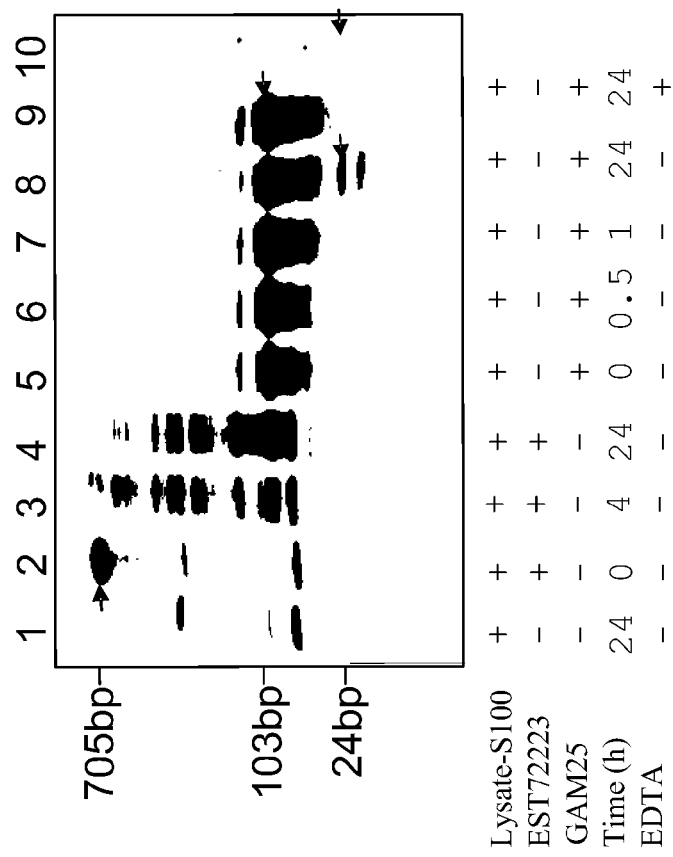

Reference is now made to FIGS. 15B, 15C and 15D that are pictures of laboratory results, which when taken together demonstrate laboratory confirmation of expression of the bioinformatically detected novel oligonucleotide of FIG. 15A. In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with either a 102 nt antisense MIR98 probe or a 145 nt antisenseGAM25 precursor transcript probe respectively. The Northern blot results of these experiments demonstrated processing of EST72223 RNA by Hela lysate (lanes 2-4, in 15B and 15C), into ~80 bp and ~22 bp segments, which reacted with the MIR98 precursor probe (15B), and into ~100 bp and ~24 bp segments, which reacted with the GAM25 precursor probe (15C). These results demonstrate the processing of EST72223 by Hela lysate into MIR98 precursor and GAM25 precursor. It is also appreciated from FIG. 15C (lane 1) that Hela lysate itself reacted with the GAM25 precursor probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 precursors into their respective mature, 'diced' segments, transcripts of MIR98 and of the bioinformatically predicted GAM25 precursors were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 precursor probes. Capped transcripts were prepared for in-vitro RNA cleavage assays with T7 RNA polymerase, including a m7G (5')ppp(5')G-capping reaction using the T7-mMessage mMachine kit (Ambion). Purified PCR products were used as template for the reaction. These were amplified for each assay with specific primers containing a T7 promoter at the 5 end and a T3 RNA polymerase promoter at the 3 end. Capped RNA transcripts were incubated at 30 C in supplemented, dialysis concentrated, Hela S100 cytoplasmic extract (4C Biotech, Seneffe, Belgium). The Hela S100 was supplemented by dialysis to a final concentration of 20 mM Hepes, 100 mM KCl, 2.5 mM MgCl2, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 g/ml creatine kinase, 25 mM creatine phosphate, 2.5 mM DTT and 50% S100 extract. Proteinase K, used to enhance Dicer activity (Zhang et al., EMBO J. 21, 5875-5885 (2002)) was dissolved in 50 mM Tris-HCl pH 8, 5 mM CaCl2, and 50% glycerol, was added to a final concentration of 0.6 mg/ml. Cleavage reactions were stopped by the addition of 8 volumes of proteinase K buffer (200 Mm Tris-Hcl, pH 7.5, 25 mM EDTA, 300 mM NaCl, and 2% SDS) and incubated at 65 C for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1×TBE-7M Urea gel.

The Northern blot results of these experiments demonstrated an accumulation of a ~22 bp segment which reacted with the MIR98 precursor probe, and of a ~24 bp segment which reacted with the GAM25 precursor probe, over time (lanes 5-8). Absence of these segments when incubated with EDTA (lane 9), which is known to inhibit Dicer enzyme (Zhang et al., 2002), supports the notion that the processing of MIR98 and GAM25 precursors into their 'diced' segments is mediated by Dicer enzyme, found in Hela lysate. Other RNases do not utilize divalent cations and are thus not inhibited by EDTA. The molecular sizes of EST72223, MIR-98 and GAM25 and their corresponding precursors are indicated by arrows.

FIG. 15D present Northern blot results of same above experiments with GAM25 probe (24 nt). The results clearly demonstrated the accumulation of mature GAM25 oligonucleotide after 24 h.

To validate the identity of the band shown by the lower arrow in FIGS. 15C and 15D, a RNA band parallel to a marker of 24 base was excised from the gel and cloned as in Elbashir et al (2001) and sequenced. 90 clones corresponded to the sequence of mature GAM25 oligonucleotide, three corresponded to GAM25* (the opposite arm of the hairpin with a 1-3 nucleotide 3 overhang) and two to the hairpin-loop.

GAM25 was also validated endogenously by sequencing from both sides from a HeLa YM100 total-RNA "ligation" libraries, utilizing hemispecific primers as described in FIG. 13.

Taken together, these results validate the presence and processing of a novel MIR-like oligonucleotide, GAM25, which was predicted bioinformatically. The processing of this novel GAM oligonucleotide product, by Hela lysate from EST72223, through its precursor, to its final form was similar to that observed for known miRNA oligonucleotide, MIR98.

Transcript products were 705nt (EST72223), 102nt (MIR98precursor), 125nt (GAM25 precursor) long. EST72223 was PCR amplified with T7-EST 72223 forward primer: 5"-TAATACGACTCACTATAGGCCCTTATTA-GAGGATTCTGCT-3" (SEQ ID NO: 59897) and T3-EST72223 reverse primer: "-AATTAACCCTCAC-TAAAGGTTTTTTTTTCCTGAGACAGAG T-3" (SEQ ID NO: 59898).MIR98 was PCR amplified using EST72223 as a template with T7MIR98 forward primer: 5-"TAATACGACT-CACTATAGGGTGAGGTAGTAAGTTGTATT GTT-3" (SEQ ID NO: 59899) and T3MIR98 reverse primer: 5"-AAT-TAACCCTCACTAAAGGGAAAGTAGTAAGTTGTATAG TT-3" (SEQ ID NO: 59900).GAM25 was PCR amplified using EST72223 as a template with GAM25 forward primer: 5"-GAGGCAGGAGAATTGCTTGA-3" (SEQ ID NO: 59901) and T3-EST72223 reverse primer:5" -AATTAAC-CCTCACTAAAGG CCTGAGACAGAGTCTTGCTC-3" (SEQ ID NO: 59902).

It is appreciated that the data presented in FIGS. 15A, 15B, 15C and 15D when taken together validate the function of the bioinformatic oligonucleotide detection engine 100 of FIG. 2. FIG. 15A shows a novel GAM oligonucleotide bioinformatically detected by the BIOINFORMATIC OLIGONUCLE-OTIDE DETECTION ENGINE 100, and FIGS. 15C and 15D show laboratory confirmation of the expression of this novel oligonucleotide. This is in accord with the engine training and validation methodology described hereinabove with reference to FIG. 3.

DETAILED DESCRIPTION OF LARGE TABLES

Table 1 comprises data relating the SEQ ID NO of oligonucleotides of the present invention to their corresponding GAM NAME, and contains the following fields: GAM SEQ-ID: GAM SEQ ID NO, as in the Sequence Listing; GAM NAME: Rosetta Genomics Ltd. nomenclature (see below); GAM RNA SEQUENCE: Sequence (5' to 3') of the mature, 'diced' GAM RNA; GAM ORGANISM: identity of the organism encoding the GAM oligonucleotide; GAM POS: Dicer cut location (see below); and Table 2 comprises detailed textual description according to the description of FIG. 1 of each of a plurality of novel GAM oligonucleotides of the present invention, and contains the following fields: GAM NAME: Rosetta Genomics Ltd. nomenclature (see below); GAM ORGANISM: identity of the organism encoding the GAM oligonucleotide; PRECUR SEQ-ID: GAM precursor Seq-ID, as in the Sequence Listing; PRECURSOR SEQUENCE: Sequence (5' to 3') of the GAM precursor; GAM DESCRIPTION: Detailed description of GAM oligonucleotide with reference to FIG. 1; and Table 3 comprises data relating to the source and location of novel GAM oligonucleotides of the present invention, and contains the following fields: GAM NAME: Rosetta Genomics Ltd. nomenclature (see below); PRECUR SEQ-ID: GAM precursor SEQ ID NO, as in the Sequence Listing; GAM ORGANISM: identity of the organism encodes the GAM oligonucleotide; SOURCE: For human GAM-chromosome encoding the human GAM oligonucleotide, otherwise—accession ID (GenBank, NCBI); STRAND: Orientation of the strand, '+' for the plus strand, '–' for the minus strand; SRC-START OFFSET: Start offset of GAM precursor sequence relative to the SOURCE; SRC-END OFFSET: End offset of GAM precursor sequence relative to the SOURCE; and Table 4 comprises data relating to GAM precursors of novel GAM oligonucleotides of the present invention, and contains the following fields: GAM NAME: Rosetta Genomics Ltd. nomenclature (see below); PRECUR SEQ-ID: GAM precursor Seq-ID, as in the Sequence Listing; GAM ORGANISM: identity of the organism encoding the GAM oligonucleotide; PRECURSOR-SEQUENCE: GAM precursor nucleotide sequence (5' to 3'); GAM FOLDED PRECUR-SOR RNA: Schematic representation of the GAM folded precursor, beginning 5' end (beginning of upper row) to 3' end (beginning of lower row), where the hairpin loop is positioned at the right part of the draw; and Table 5 comprises data relating to GAM oligonucleotides of the present invention, and contains the following fields: GAM NAME: Rosetta Genomics Ltd. nomenclature (see below); GAM ORGANISM: identity of the organism encoding the GAM oligonucleotide; GAM RNA SEQUENCE: Sequence (5' to 3') of the mature, 'diced' GAM RNA; PRE-CUR SEQ-ID: GAM precursor Seq-ID, as in the Sequence Listing; GAM POS: Dicer cut location (see below); and Table 6 comprises data relating SEQ ID NO of the GAM target gene binding site sequence to TARGET gene name and target binding site sequence, and contains the following fields: TARGET BINDING SITE SEQ-ID: Target binding site SEQ ID NO, as in the Sequence Listing; TARGET ORGANISM: identity of organism encode the TARGET gene; TARGET: GAM target gene name; TARGET BIND-ING SITE SEQUENCE: Nucleotide sequence (5' to 3') of the target binding site; and Table 7 comprises data relating to target-genes and binding sites of GAM oligonucleotides of the present invention, and contains the following fields: GAM NAME: Rosetta Genomics Ltd. nomenclature (see below); GAM ORGANISM: identity of the organism encoding the GAM oligonucleotides; GAM RNA SEQUENCE: Sequence (5' to 3') of the mature, 'diced' GAM RNA; TARGET: GAM target gene name; TARGET REF-ID: Target accession number (GenBank); TARGET ORGANISM: identity of organism encode the TARGET gene; UTR: Untranslated region of binding site/s (3" or 5"); TARGET BS-SEQ: Nucleotide sequence (5' to 3') of the target binding site; BINDING-SITE-DRAW: Schematic representation of the binding site, upper row represent 5' to 3' sequence of the target, Lower row represent 3' to 5' Sequence of the GAM; GAM POS: Dicer cut location (see below); and Table 8 comprises data relating to functions and utilities of novel GAM oligonucleotides of the present invention, and contains the following fields: GAM NAME: Rosetta Genomics Ltd. nomenclature (see below); GAM RNA SEQUENCE: Sequence (5' to 3') of the mature, 'diced' GAM RNA; GAM ORGANISM: identity of the organism encoding the GAM oligonucleotide; TARGET: GAM target gene name; TARGET ORGANISM: identity of organism encode the TARGET gene; GAM FUNCTION: Description of the GAM functions and utilities; GAM POS: Dicer cut location (see below); and Table 9 comprises data of gene function references—Bibliography and contains the following fields: GAM NAME: Rosetta Genomics Ltd. nomenclature (see below); GAM RNA SEQUENCE: Sequence (5' to 3') of the mature, 'diced' GAM RNA gene; GAM ORGANISM: identity of the organism encoding the GAM oligonucleotide; TARGET: GAM target gene name; TARGET ORGANISM: identity of organism encode the TARGET gene; REFERENCES: list of references relating to the target gene; GAM POS: Dicer cut location (see below); and Table 10 comprises data relating to novel GR (Genomic Record) polynucleotides of the present invention, and contains the following fields: GR NAME: Rosetta Genomics Ltd. nomenclature (see below); GR ORGANISM: identity of the organism encoding the GR polynucleotide; GR DESCRIPTION: Detailed description of a GR gene cluster, with reference to FIG. 9; and The following conventions and abbreviations are used in the tables: The nucleotide 'U' is represented as 'T' in the tables, and GAM NAME or GR NAME are names for nucleotide sequences of the present invention given by RosettaGenomics Ltd. nomenclature method. All GAMs/GRs are designated by GAMx/GRx where x is a unique ID.

GAM POS is a position of the GAM RNA on the GAM PRECURSOR RNA sequence. This position is the Dicer cut location: A indicates a probable Dicer cut location; B indicates an alternative Dicer cut location.

All human nucleotide sequences of the present invention as well as their chromosomal location and strand orientation are derived from sequence records of UCSC-hg16 version, which is based on NCBI, Build34 database (April, 2003).

All bacteria sequences of the present invention as well as their genomic location are derived from NCBI, RefSeq database.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07842800B2). An electronic copy of the "Sequence Listing" will also be available from the USPTO upon request and payment of the fee set forth in 37 CFR 1.19(b)(3).

The invention claimed is:

1. An isolated nucleic acid selected from the group consisting of:
   (a) SEQ ID NO: 55663;
   (b) a DNA encoding the nucleic acid of (a), wherein the DNA is identical in length to (a); and
   (c) the complement of (a) or (b), wherein the complement is identical in length to the nucleic acid of (a) or (b).

2. A vector comprising a human insert, wherein the human insert consists of the nucleic acid of claim 1, and wherein the vector comprises no insert other than the nucleic acid of claim 1.

3. An oligonucleotide probe of 16-120 nucleotides in length, wherein the probe comprises the nucleic acid of claim 1.

4. An isolated nucleic acid selected from the group consisting of:
   (a) SEQ ID NO: 1485;
   (b) a DNA encoding the nucleic acid of (a), wherein the DNA is identical in length to (a); and
   (c) the complement of (a) or (b), wherein the complement is identical in length to the nucleic acid of (a) or (b).

5. A vector comprising a human insert, wherein the insert consists of the nucleic acid of claim 4, and wherein the vector comprises no other insert but the nucleic acid of claim 4.

6. An oligonucleotide probe of 16-120 nucleotides in length, wherein the probe comprises the nucleic acid of claim 4.

* * * * *